(12) United States Patent
Borremans et al.

(10) Patent No.: US 11,890,094 B2
(45) Date of Patent: Feb. 6, 2024

(54) ILLUMINANT CORRECTION FOR A SPECTRAL IMAGER

(71) Applicant: Spectricity, Mechelen (BE)

(72) Inventors: Jonathan Borremans, Lier (BE); Maarten De Bock, Ghent (BE); Jakub Raczkowski, Bertem (BE)

(73) Assignee: Spectricity, Mechelen (BE)

( * ) Notice: Subject to any disclaimer, the term of this patent is extended or adjusted under 35 U.S.C. 154(b) by 16 days.

(21) Appl. No.: 17/809,998

(22) Filed: Jun. 30, 2022

(65) Prior Publication Data

US 2022/0346672 A1 Nov. 3, 2022

Related U.S. Application Data

(63) Continuation-in-part of application No. 17/170,127, filed on Feb. 8, 2021, now Pat. No. 11,493,387.
(Continued)

(51) Int. Cl.
*G01J 3/02* (2006.01)
*A61B 5/1455* (2006.01)
(Continued)

(52) U.S. Cl.
CPC ............ *A61B 5/1455* (2013.01); *A61B 5/443* (2013.01); *G06N 3/067* (2013.01); *G06N 3/08* (2013.01);
(Continued)

(58) Field of Classification Search
CPC ....... A61B 2562/0238; A61B 2562/046; G01J 2003/1226; G01J 3/0297; G01J 3/28; G01J 3/2803; G01J 3/51; G06N 3/0499
See application file for complete search history.

(56) References Cited

U.S. PATENT DOCUMENTS

| 2012/0035442 A1* | 2/2012 | Barman ................. G01J 3/0208 600/316 |
| 2020/0375521 A1* | 12/2020 | Hadoux ................... A61B 3/12 |
| 2021/0010862 A1* | 1/2021 | Raz ....................... H04N 25/134 |

FOREIGN PATENT DOCUMENTS

| CA | 2954625 A1 | 12/2015 |
| CN | 105593651 A | 5/2016 |

(Continued)

OTHER PUBLICATIONS

Pichette et al.; Hyperspectral Calibration Method For CMOS-based Hyperspectral Sensors; Proc. SPIE 10110, Photonic Instrumentation Engineering IV, Feb. 20, 2017; 14 pgs; https://doi.org/10.1117/12.2253617.
(Continued)

*Primary Examiner* — Abdullahi Nur
(74) *Attorney, Agent, or Firm* — Garlick & Markison; Kelly H. Hale

(57) ABSTRACT

A sensor system includes an array of optical sensors on an integrated circuit and a plurality of sets of optical filters atop at least a portion of the array. Each set of optical filters is associated with a set of optical sensors of the array, with a set of optical filters including a plurality of optical filters, with each optical filter being configured to pass light in a different wavelength range. A first interface is configured to interface with the optical sensors and first processing circuitry that is configured to execute operational instructions for receiving an output signal representative of received light from the optical sensors and determining a spectral response for each set of optical sensors. A second interface is configured to interface with the first processing circuitry with second processing circuitry that is configured for determining, based on the spectral response for each set of optical sensors, an illuminant spectrum for each spectral (Continued)

response and then substantially remove the illuminant spectrum from the spectral response.

20 Claims, 17 Drawing Sheets

Related U.S. Application Data

(60) Provisional application No. 63/364,408, filed on May 9, 2022, provisional application No. 62/988,759, filed on Mar. 12, 2020.

(51) Int. Cl.
*G06N 3/08* (2023.01)
*A61B 5/00* (2006.01)
*G06N 3/067* (2006.01)

(52) U.S. Cl.
CPC . *A61B 2562/0238* (2013.01); *A61B 2562/046* (2013.01)

(56) References Cited

FOREIGN PATENT DOCUMENTS

| | | |
|---|---|---|
| CN | 106840398 A | 6/2017 |
| WO | 2018056976 A1 | 3/2018 |
| WO | 2019180571 A1 | 9/2019 |

OTHER PUBLICATIONS

China National Intellectual Property Administration; Search Report; dated Aug. 25, 2023; 3 pgs.

* cited by examiner

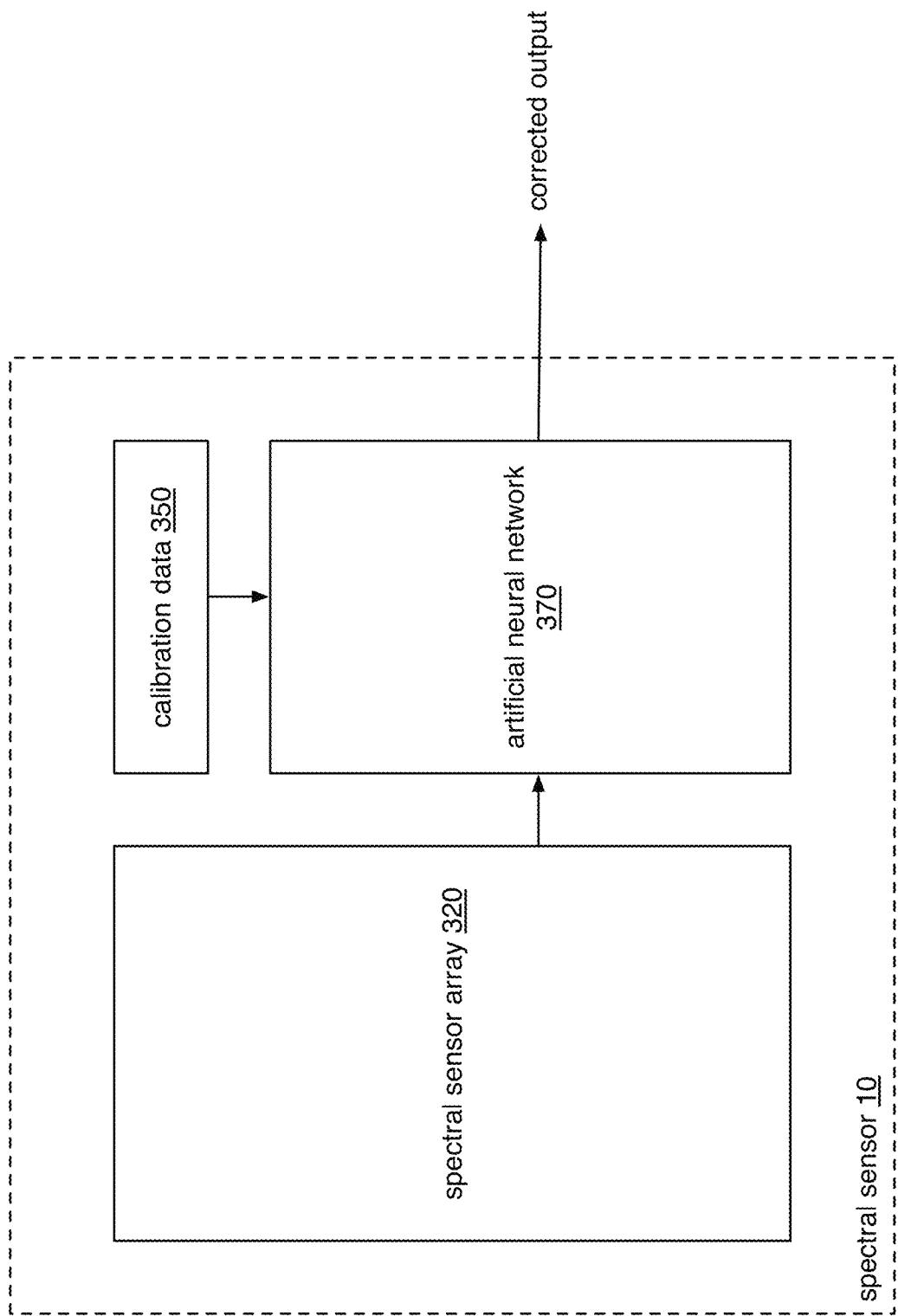

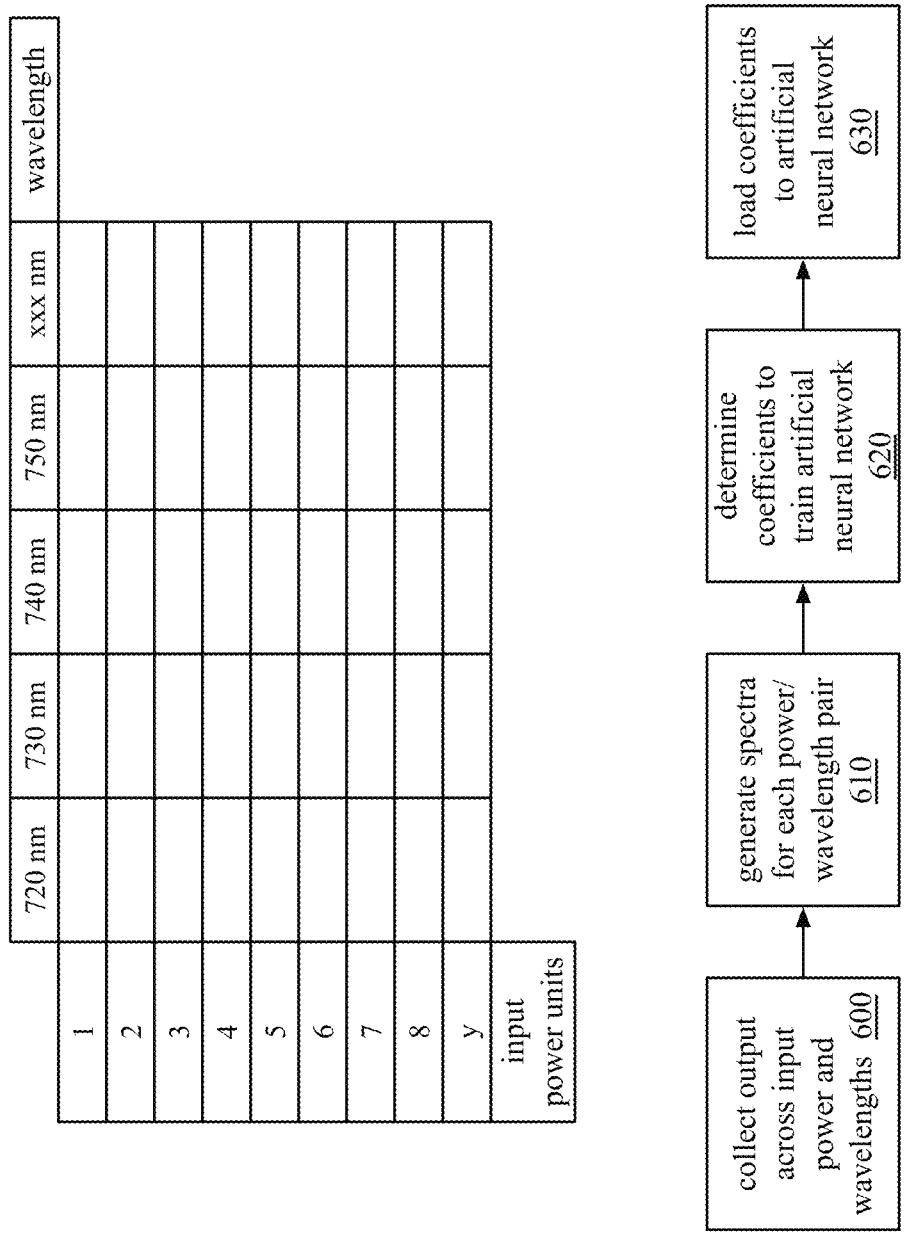

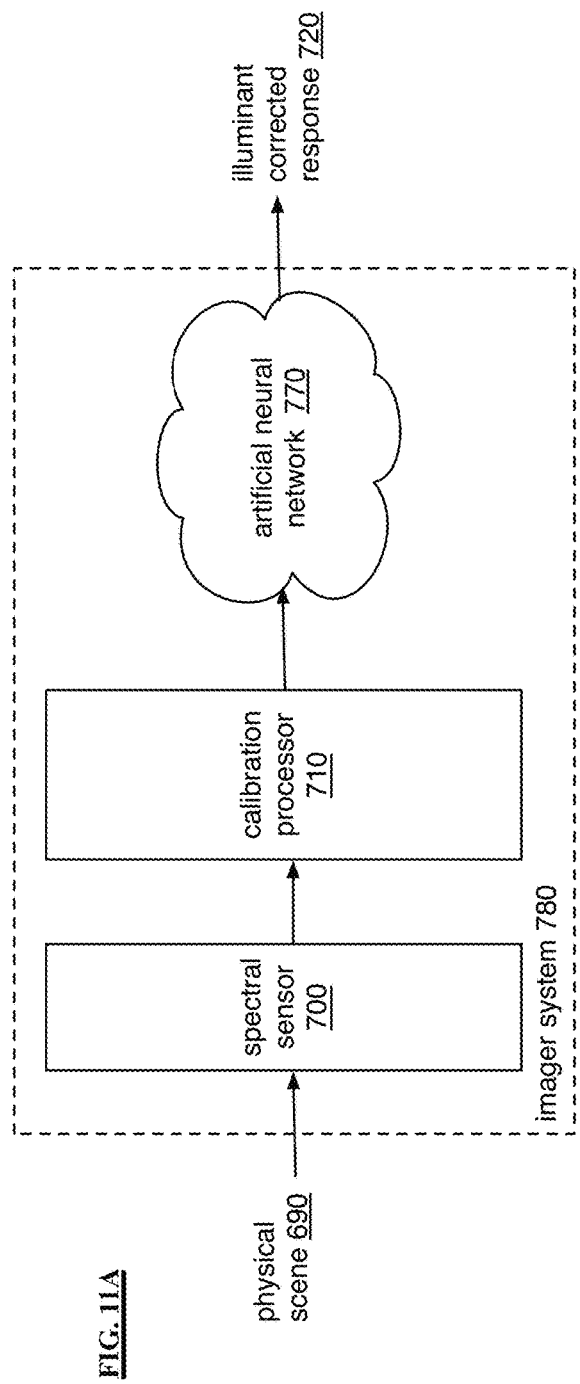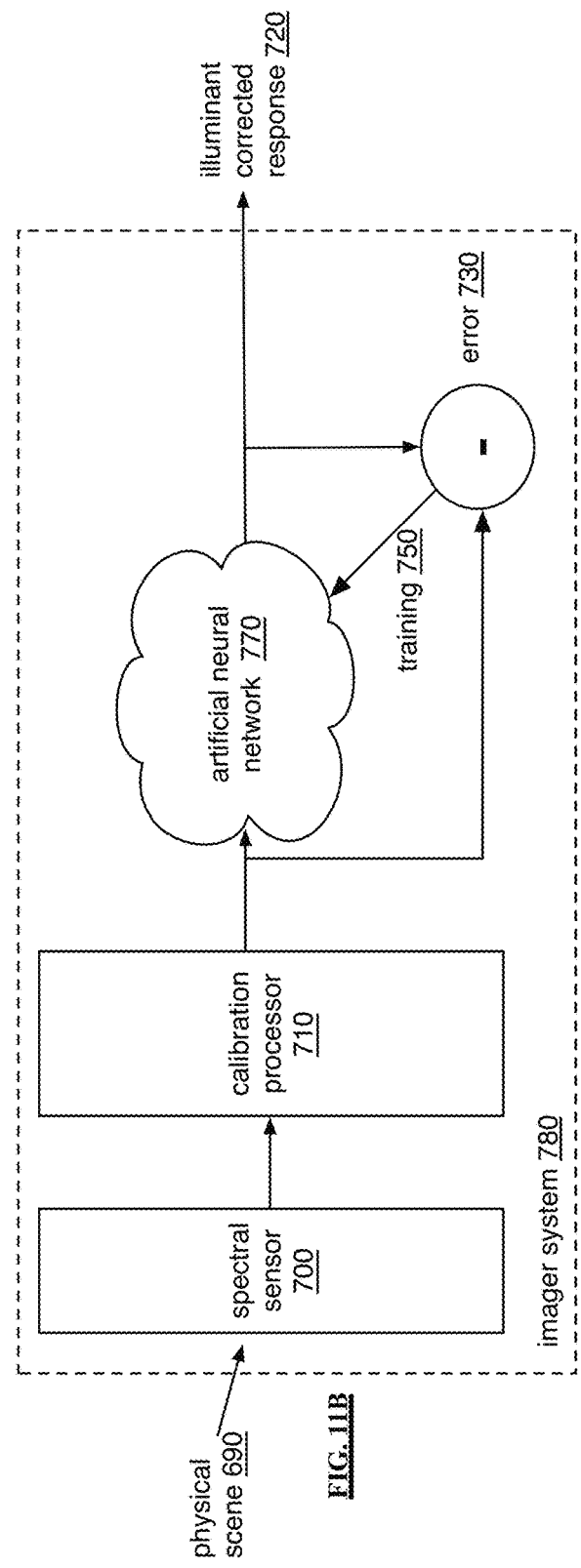

ILLUMINANT CORRECTION FOR A SPECTRAL IMAGER

CROSS REFERENCE TO RELATED PATENTS

The present U.S. Utility Patent Application claims priority pursuant to 35 U.S.C. § 120, as a continuation-in-part (CIP) of U.S. Utility application Ser. No. 17/170,127, entitled "CORRECTION AND CALIBRATION OF SPECTRAL SENSORS" filed Feb. 8, 2021, which claims priority pursuant to 35 U.S.C. § 119(e) to U.S. Provisional Application No. 62/988,759, entitled "CORRECTION AND CALIBRATION OF SPECTRAL SENSORS," filed Mar. 12, 2020, both of which are hereby incorporated herein by reference in their entirety and made part of the present U.S. Utility Patent Application for any and all purposes.

The present U.S. Utility Patent Application also claims priority pursuant to 35 U.S.C. § 119(e) to U.S. Provisional Application No. 63/364,408, entitled "ILLUMINANT CORRECTION FOR A SPECTRAL IMAGER", filed May 9, 2022.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

BACKGROUND OF THE INVENTION

Technical Field of the Invention

This invention relates generally to spectroscopy and more particularly to spectrum correction for spectral sensors using interference-based filters.

Spectroscopy devices have proven to be useful for applications in various industries including, for example, health, biometrics, agriculture, chemistry and fitness. In general, spectroscopy devices function by detecting and/or acquiring incident light relating to multiple ranges of wavelengths and extracting spectral information. Interference-based filters, such as Fabry-Pérot filters, when used in conjunction with spectral sensors have been shown to be capable of providing controlled light wavelengths.

As is further known, light traveling through interference-based filters is subject to various non-ideal conditions, along with nonideal sensor performance, any of which can have a negative effect on the performance of a given spectroscopy device.

DESCRIPTION OF RELATED ART

Brief Description of the Several Views of the Drawing(s)

FIG. 1A provides a top-down illustration of an example optical sensor overlaid with filters in accordance with the present invention;

FIG. 1B provides a side-view illustration of an example optical sensor overlaid with filters in accordance with the present invention;

FIG. 2 illustrates the example filter responses of a CMOS sensor overlaid with filters;

FIG. 3 provides an illustration of a comparison of raw output data and the ideal output data of an example spectral sensor;

FIG. 4 is a schematic block diagram of an embodiment of a spectral sensor in accordance with the present invention;

FIG. 5A provides a schematic block diagram of an embodiment of a spectral sensor incorporating an artificial neural network in accordance with the present invention;

FIG. 5B provides a schematic block diagram of another embodiment of a spectral sensor incorporating an artificial neural network in accordance with the present invention;

FIG. 6A provides a simplified illustration of an artificial neural network incorporated in a spectral sensor in accordance with the present invention;

FIG. 6B provides a simplified illustration of a multi-layer artificial neural network in accordance with the present invention;

Figure 7B:
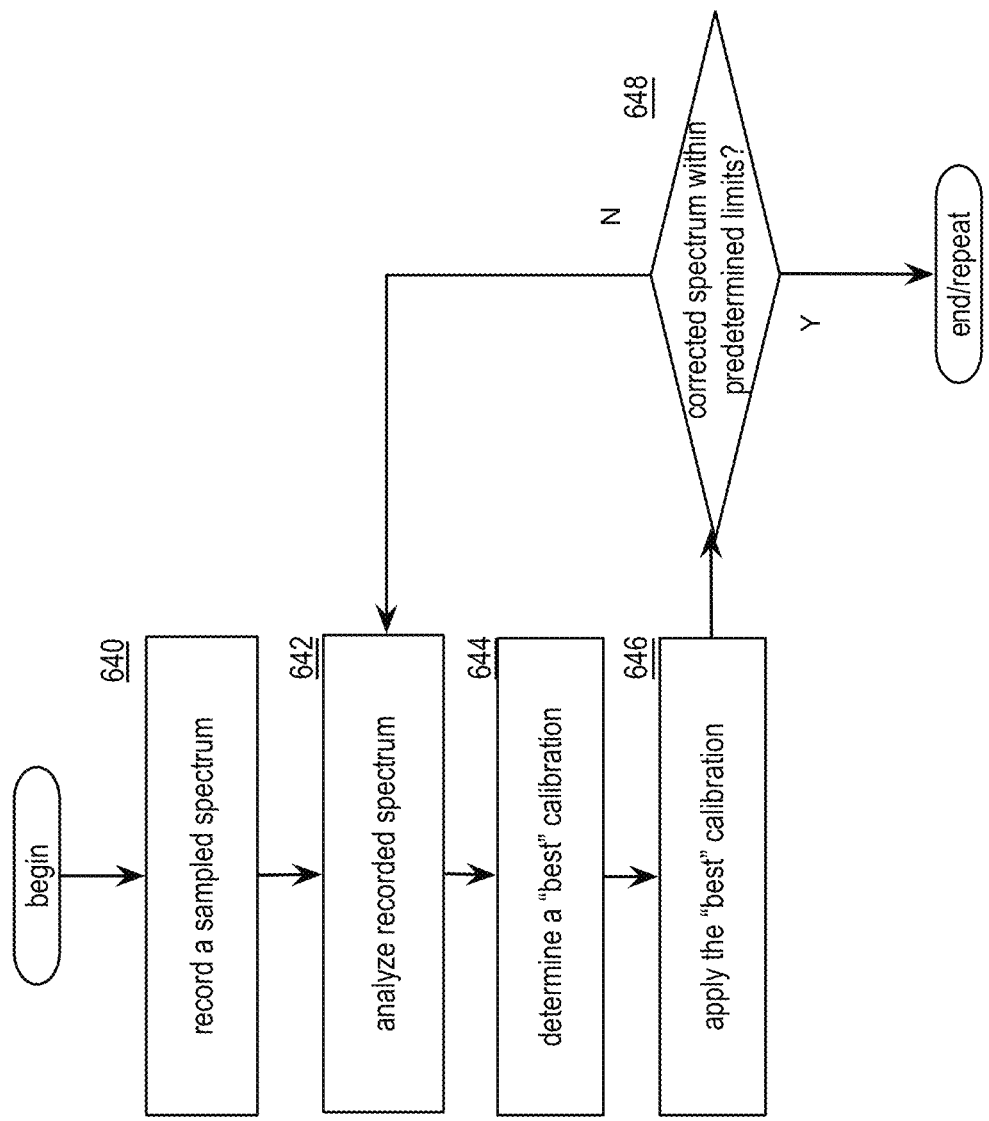
FIG. 7B is a logic diagram illustrating an example method for adaptively correcting the spectral output from a sensor array in accordance with the present invention.
Figure 7C:
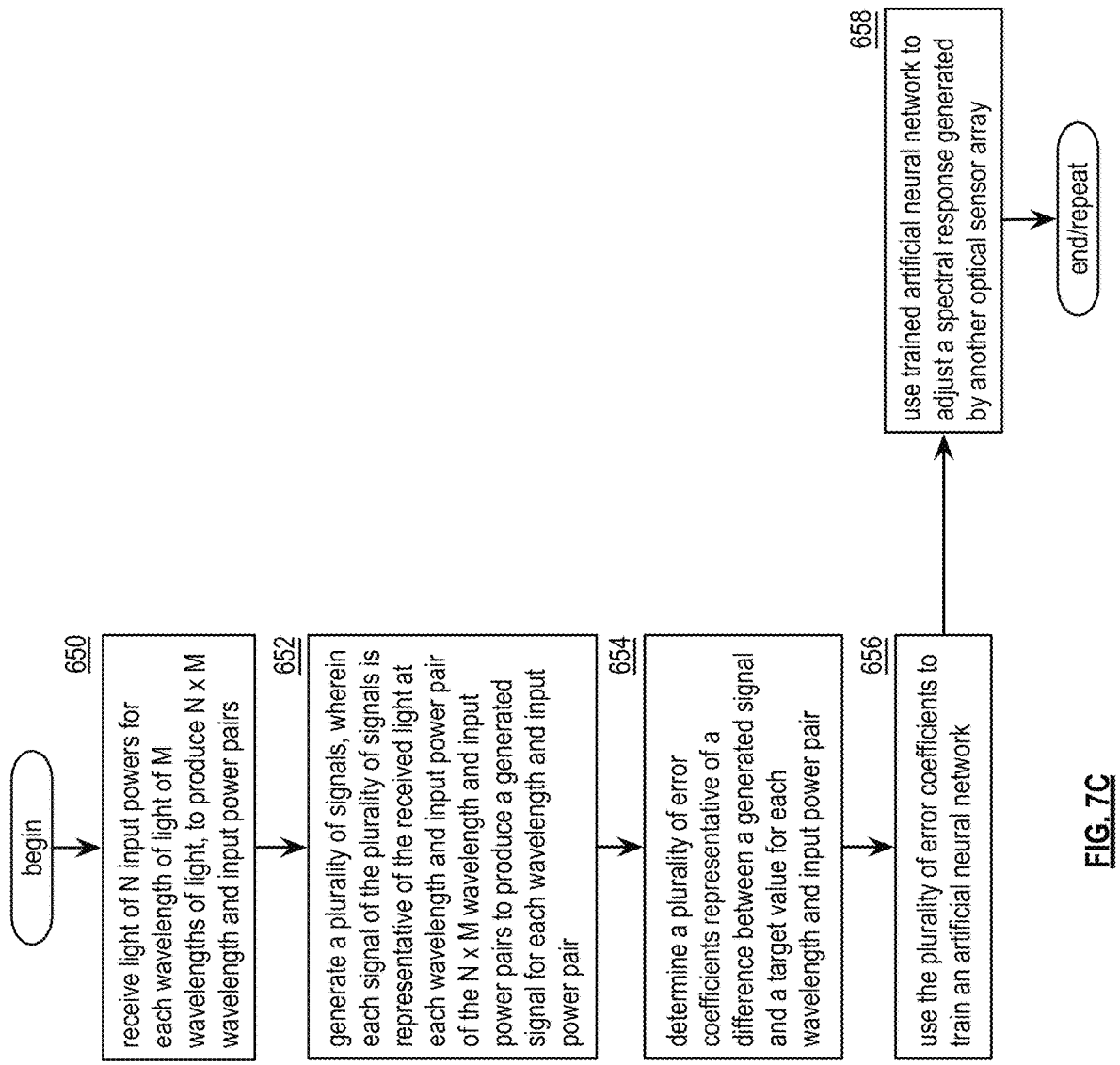
FIG. 7A is a logic diagram illustrating an example method for correcting the raw spectral output into corrected spectra in accordance with the present invention.
Figure 8A:
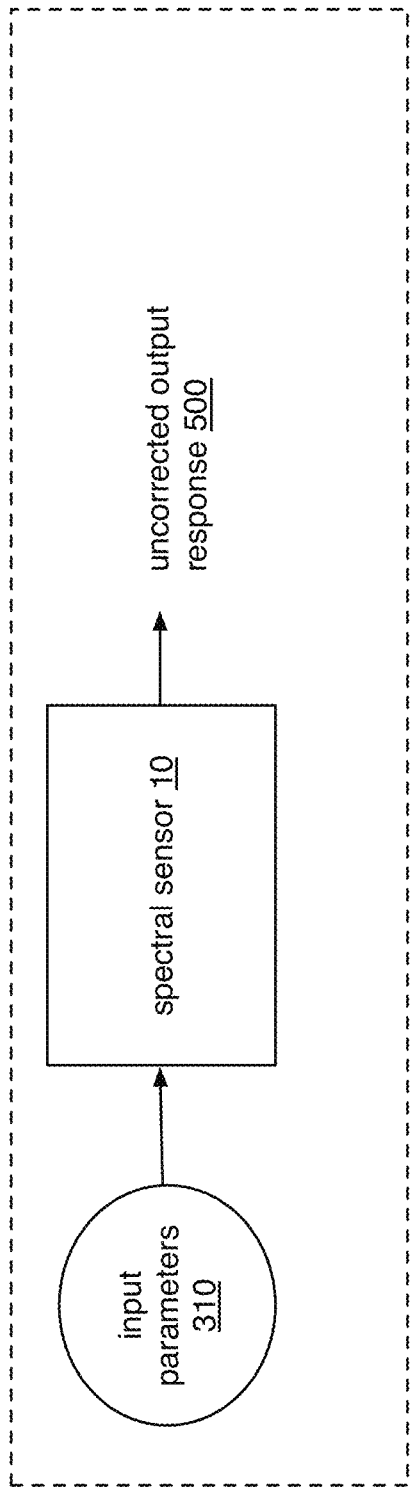
Figure 8B:
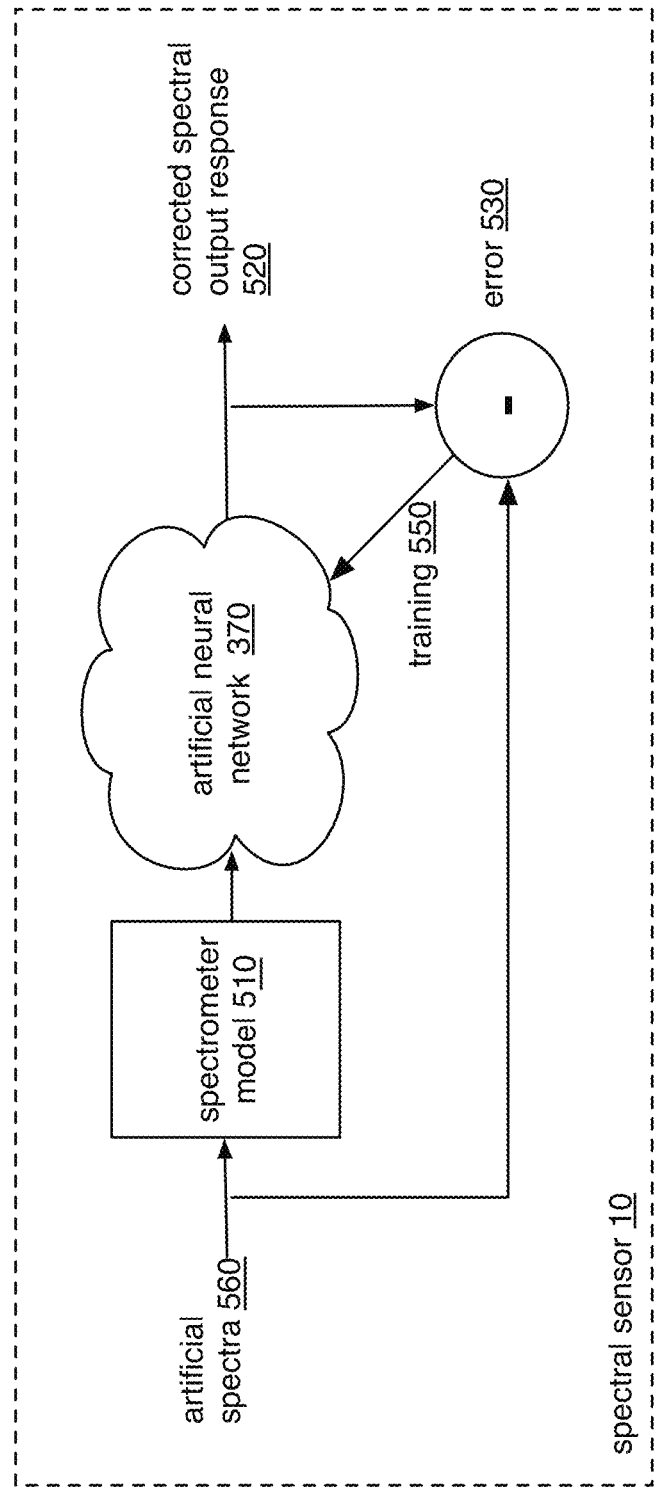
Figure 8C:
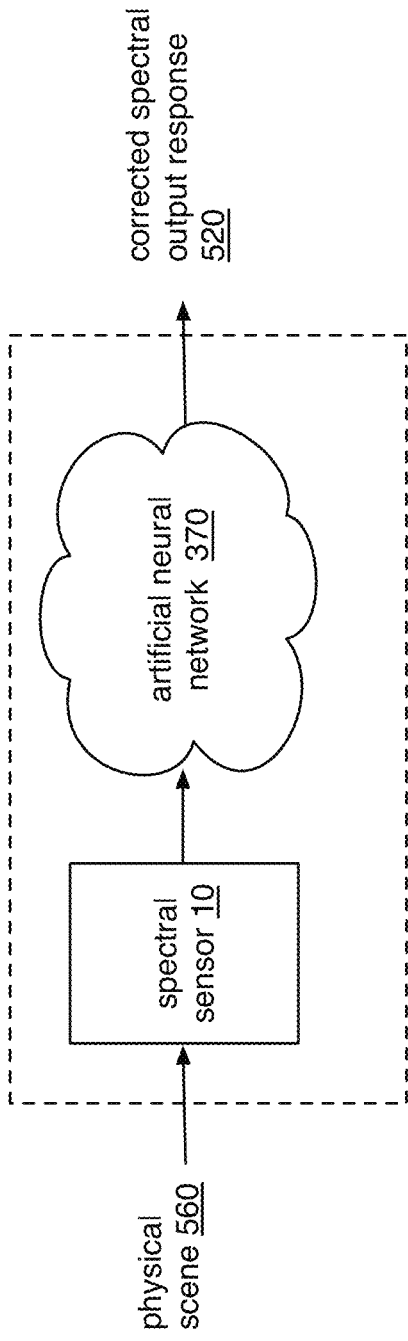
Figure 8D:
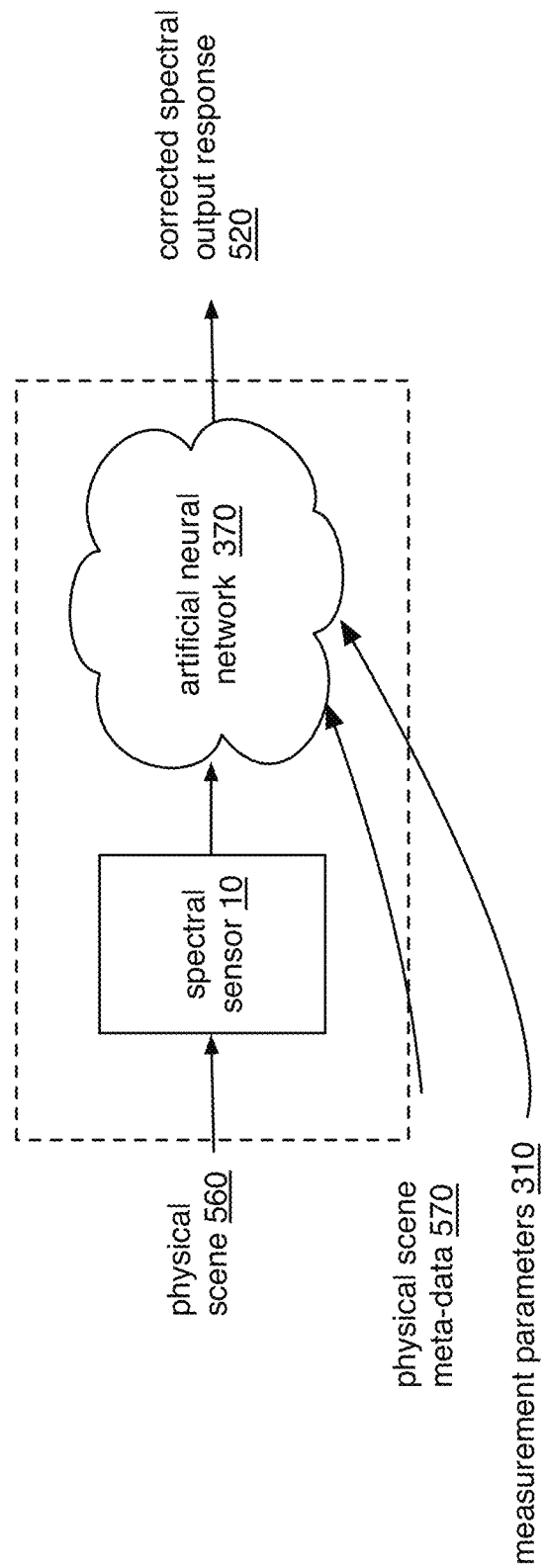
Figure 9:
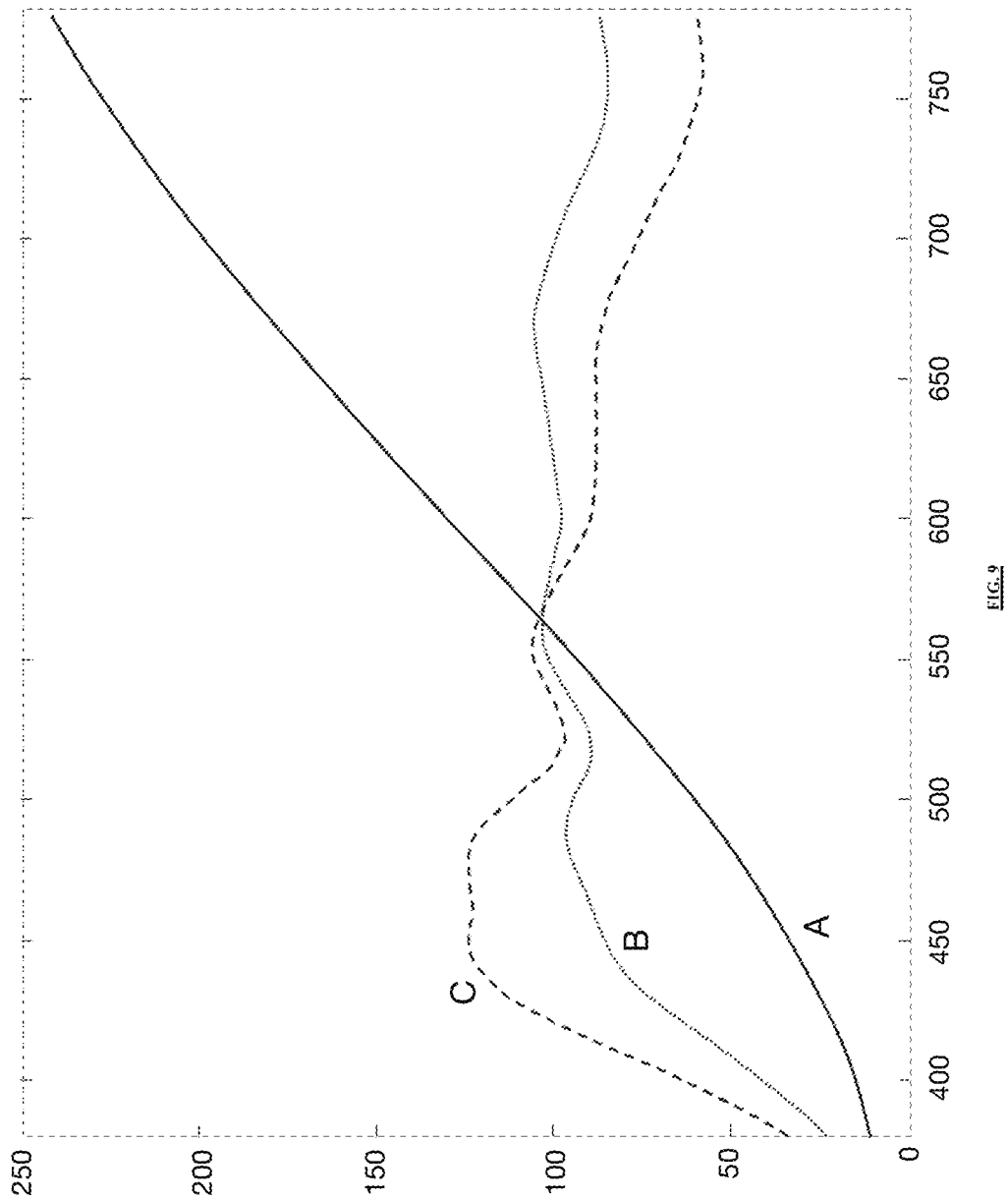
Figure 10:
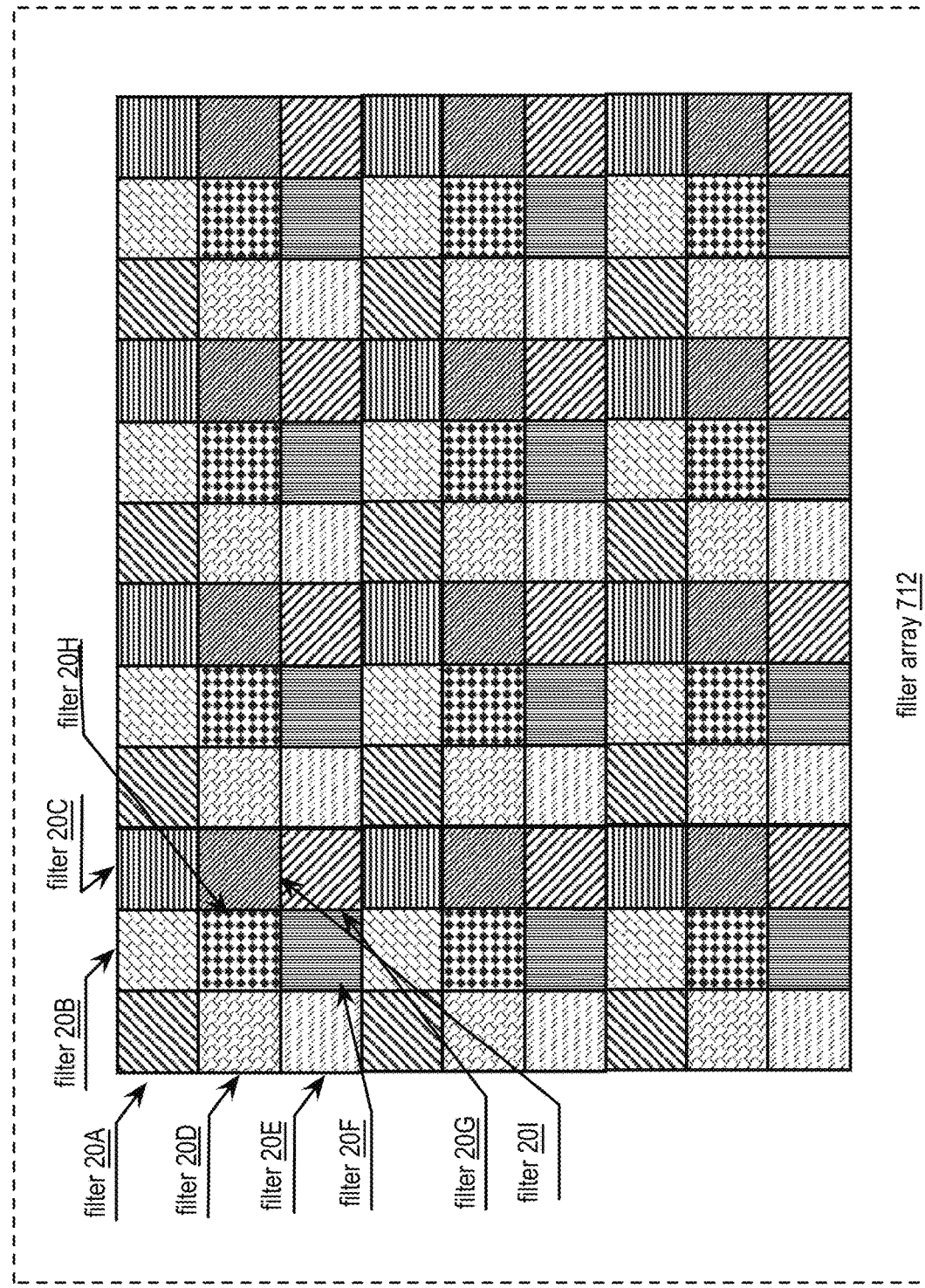
Figure 11C:
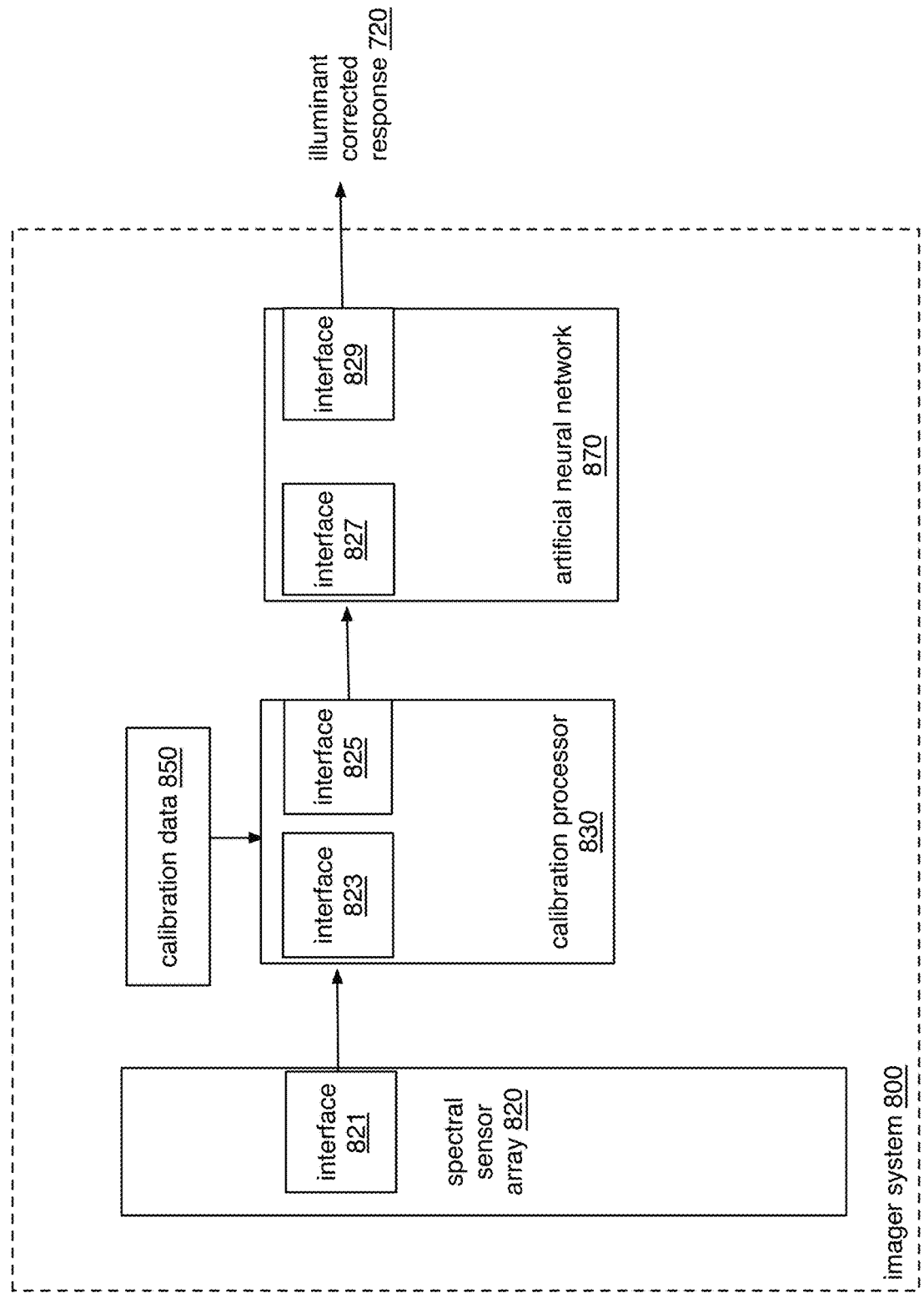
Figure 12:
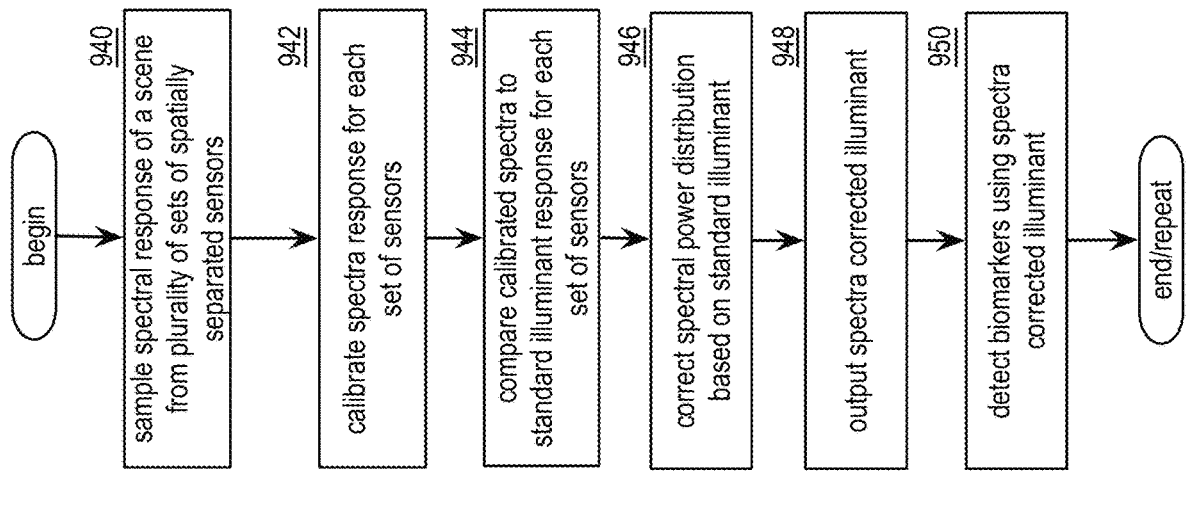

FIG. 7C provides logic diagram illustrating another example method for adaptively correcting the spectral output from a sensor array in accordance with the present invention;

FIG. 8A provides an illustration of an example spectral sensor where a sweep of monochromatic light and input power are provided in accordance with the present invention;

FIG. 8B provides an illustration of an example spectral sensor incorporating an artificial neural network in accordance with the present invention;

FIG. 8C provides an illustration of an example of a physical scene provided to a spectral sensor and output to a trained artificial neural network in accordance with the present invention;

FIG. 8D provides an illustration of an example spectral sensor where meta-data of a physical scene is provided to the artificial neural network in accordance with the present invention;

FIG. 9 provides an illustration of relative spectral power distributions for three hypothetical illuminants A, B & C across a visible spectrum;

FIG. 10 provides a top-down illustration of a filter array in accordance with the present invention;

FIG. 11A illustrates an example imager system in accordance with the present invention;

FIG. 11B illustrates an example spectral sensor where calibrated spectral response data is provided to train an artificial neural network in accordance with the present invention;

FIG. 11C provides a schematic block diagram of an embodiment of an imager system in accordance with the present invention; and FIG. 12 is a logic diagram illustrating a method for producing illuminant corrected spectra for an array of optical sensors in accordance with the present invention.

DETAILED DESCRIPTION OF THE INVENTION

Figure 1:
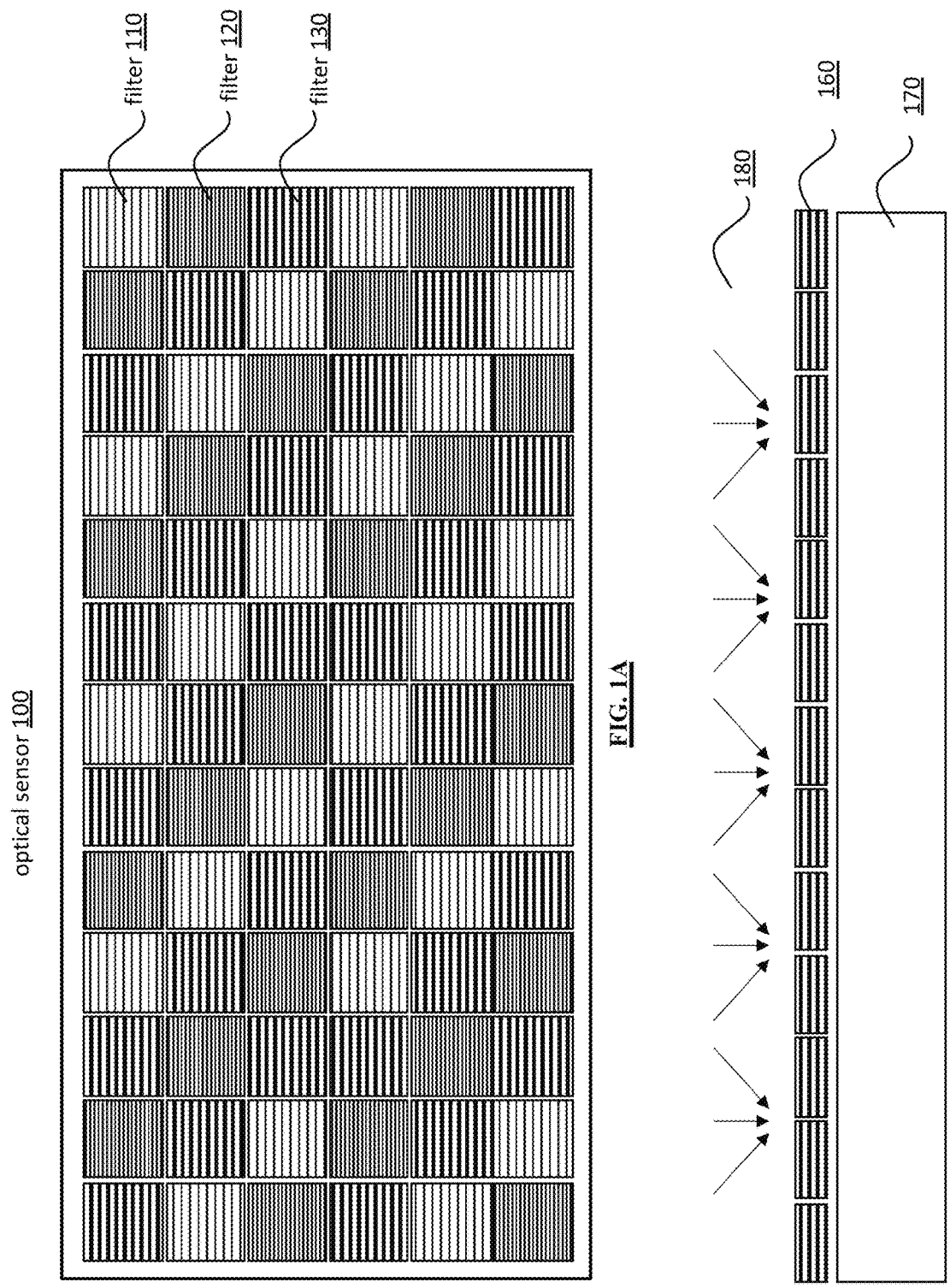

In various embodiments, spectral sensors are combined with interference filters to provide spectral information"

about a scene and/or light source. Interference based filters, such as Fabry-Pérot filters, can exhibit non-ideal filter response to an underlying sensor. For example, filter response can include cross talk between filters, undesirable second order responses to incident light, angular dependencies to incident light and incident light can include light from sources not intended to be evaluated. Sensors themselves can also exhibit non-ideal performance, including non-linearities, cross talk, electronic noise, etc. FIG. 1A provides a top-down illustration of an example integrated optical sensor 100 overlaid with filters 110, 120 and 130 optimized for one of three spectral bands, respectively. As shown filters 110, 120 and 130 repeat as an array across the surface of optical sensor 100. Alternatively, filters 110, 120 and 130 could repeat using a different pattern or even in a random pattern to pass filter responses to sensors underlying the filter array. In an example (not shown) spectral bands exceeding 3 could be used to overlay sensors as desired in any practical orientation. In an embodiment optical sensor 100 is an example of a spectral sensor useful for diffuse optical spectroscopy, where arrays of spectral filters are associated with optical sensors to provide diffuse spectral sensing. FIG. 1B provides a side-view illustration of an example optical sensor overlaid with a filter array. In the example, incident light 180 is directed sensor array 170 through filter array 160.

Ideally the filters of the integrated optical sensor in FIGS. 1A and 1B would pass only incident light within the desired spectral wavelengths to the underlying sensor, such that an ideal sensor could then output filter responses that exactly represent the spectrum of the incident light. In practice, neither the interference filters nor the sensors are ideal, thus when the output of a given optical sensor, such as that illustrated in FIGS. 1A and 1B is measured, the resulting spectrum is unlikely to correctly represent the spectrum of the incident light. Indeed, the resulting spectrum can exhibit a nonlinear relationship to input light intensity, spectrum of an object under measurement, and/or illumination spectrum of the input light. Moreover, errors associated with manufacturing, such as manufacturing tolerances and uniformity between integrated optical sensors, such as integrated optical sensor 100, can contribute to non-deal performance.

Figure 2:
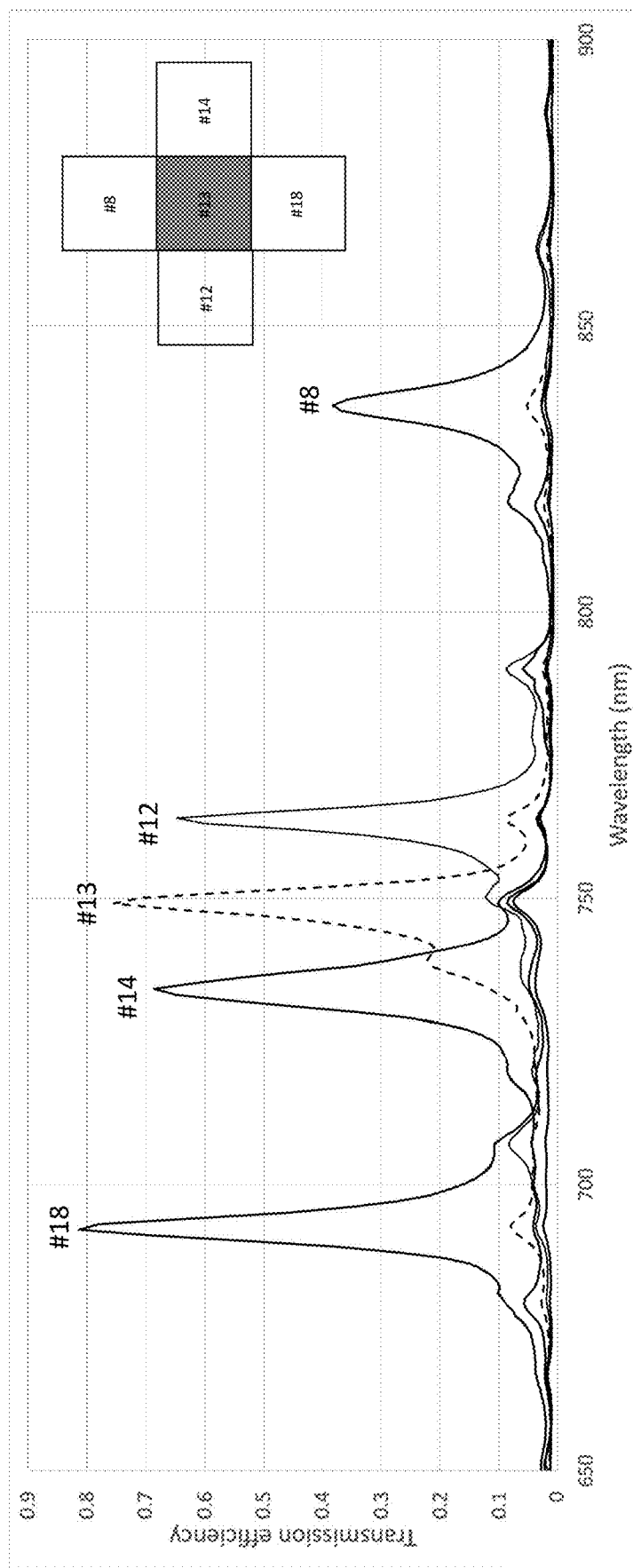

FIG. 2 illustrates the filter responses of a CMOS sensor (in this case using Fabry-Pérot filters) exhibiting crosstalk from neighboring sensors. In an ideal sensor the filter response of a particular sensor pixel, such as that of pixel #13, would come only from pixel #13, without contributing to other pixels within the array. As illustrated, neighboring pixels #8, #12, #14 and #18 exhibit at least some unwanted response from wavelength centered on pixel #13, along with other non-idealities. Reconstruction of a "clean" output spectrum (one that adequately represents the spectrum of the incident light on the optical sensor) is non-trivial, even when the exhibited filter response shapes are known. In the illustration of FIG. 2, the responses are not reflective of perfect "Fabry-Pérot" responses, and the generation of crosstalk from the adjacent filters is problematic, adding to the response error. Considering that each pixel can suffer non-ideal responses and crosstalk error, it can be readily understood that correction and or calibration of a given optical sensor can become exceedingly difficult and/or imprecise. Additionally, material properties of the filters themselves, quality differences and part-to part differentials provide additional complexity.

Figure 3:
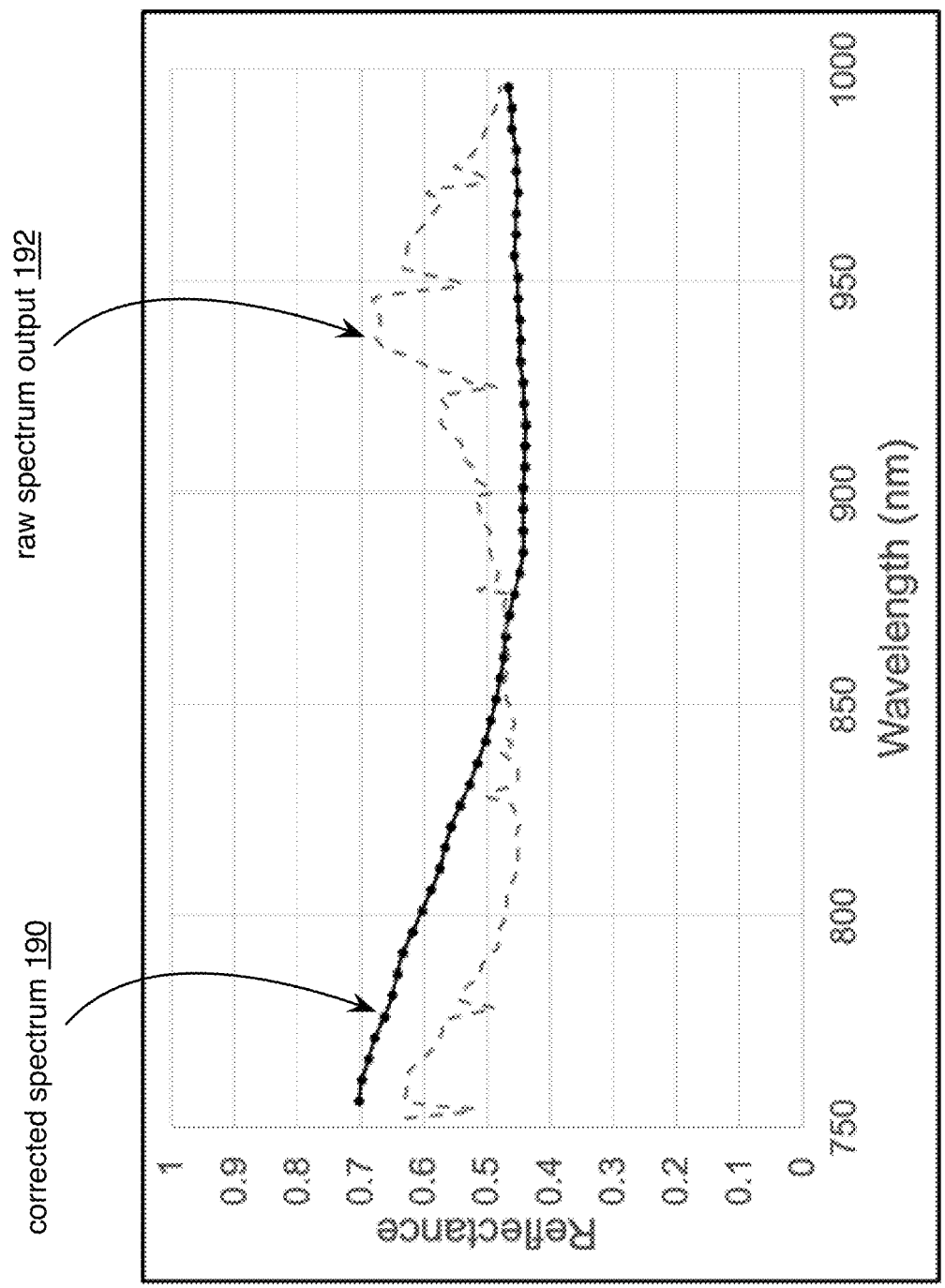

FIG. 3 provides an illustration of the raw output data 190 of a reflectance measurement (filter response) from approximately 740 to 1020 nm of an exemplary optical sensor, along with an ideal or "corrected" spectrum 192 for the measurement. In the example, the raw output data cannot be adapted with a complex correction exercise to transform it into a "real" spectrum (i.e. a spectrum representative of the spectrum of the incident light be evaluated).

In an example, the raw output of a spectral sensor $O_{RAW}$ can be measured, as a matrix of [1×N] values. It can be corrected by a matrix multiplication such that:

$$O = O_{RAW} \times C$$

with O being the corrected spectrum and C [N×M] is a correction matrix with M being the desired output wavelength response(s) (in a linear correction step). C is a "correction matrix" constructed from measured and/or derived knowledge of the sensor and filters, or factory measurement/calibration of the filter characteristics of the sensor or a combination of both.

In an example, $O_{RAW}$ is built from N (e.g. with N=64 in a 64-channel spectrometer built out of N photosensitive elements and N filters on top of the elements) values from the filter outputs. In the example of FIG. 3, the 64 outputs are limited to the sensor outputs and represent the full integrated response of each individual filter on each photodiode. Referring to FIG. 1A, a spectral sensor can include a plurality of optical sensors with a plurality of sets of optical filters configured as a layer having a top surface and a bottom surface located atop the plurality of optical sensors. In the example, a set of optical filters of the plurality of sets of optical filters includes a plurality of optical filters, where each optical filter of the plurality of optical filters is configured to pass light in a different wavelength range. In an example, a plurality of optical filters configured to pass light in the same wavelength range can be provided in an array, such that in a given array each wavelength range is represented redundantly. Myriad layout options for the optical filters are possible. In a specific example, the optical filters of each set of optical filters can be arranged in a pattern that is repeated across a sensor array. In another example, each set of optical filters can be configured in multiple disparate patterns within the same sensor array. Accordingly, due at least in part to the non-idealities discussed with reference to FIGS. 1A, 1B and FIG. 2, each of the plurality of optical filters configured to pass light in the same wavelength range can behave differently.

Referring again to FIG. 3, a given sensor output will not necessarily contain the full impact of the spectral responses from each filter on the sensor, which behavior (as seen in FIG. 2 above) is exceedingly complex and cannot be captured adequately in just 64 sampled datapoints. Additionally, the other non-idealities associated with the sensor are not captured in the output, including, for example, its inherent nonlinearities and the non-linearities affecting crosstalk, among others. Accordingly, providing a single correction matrix capable of providing a corrected spectrum across all conditions of input power, illumination spectral profile and scene spectral profile can be difficult, if not mathematically impossible. In an example, the correction matrix C from the equation above is "optimized" using a least squares approach to provide desired and/or expected spectral profiles in spectral measurements. More complex mathematical correction matrices can be built but, as illustrated, they can represent an exceedingly complex mathematical problem.

Figure 4:
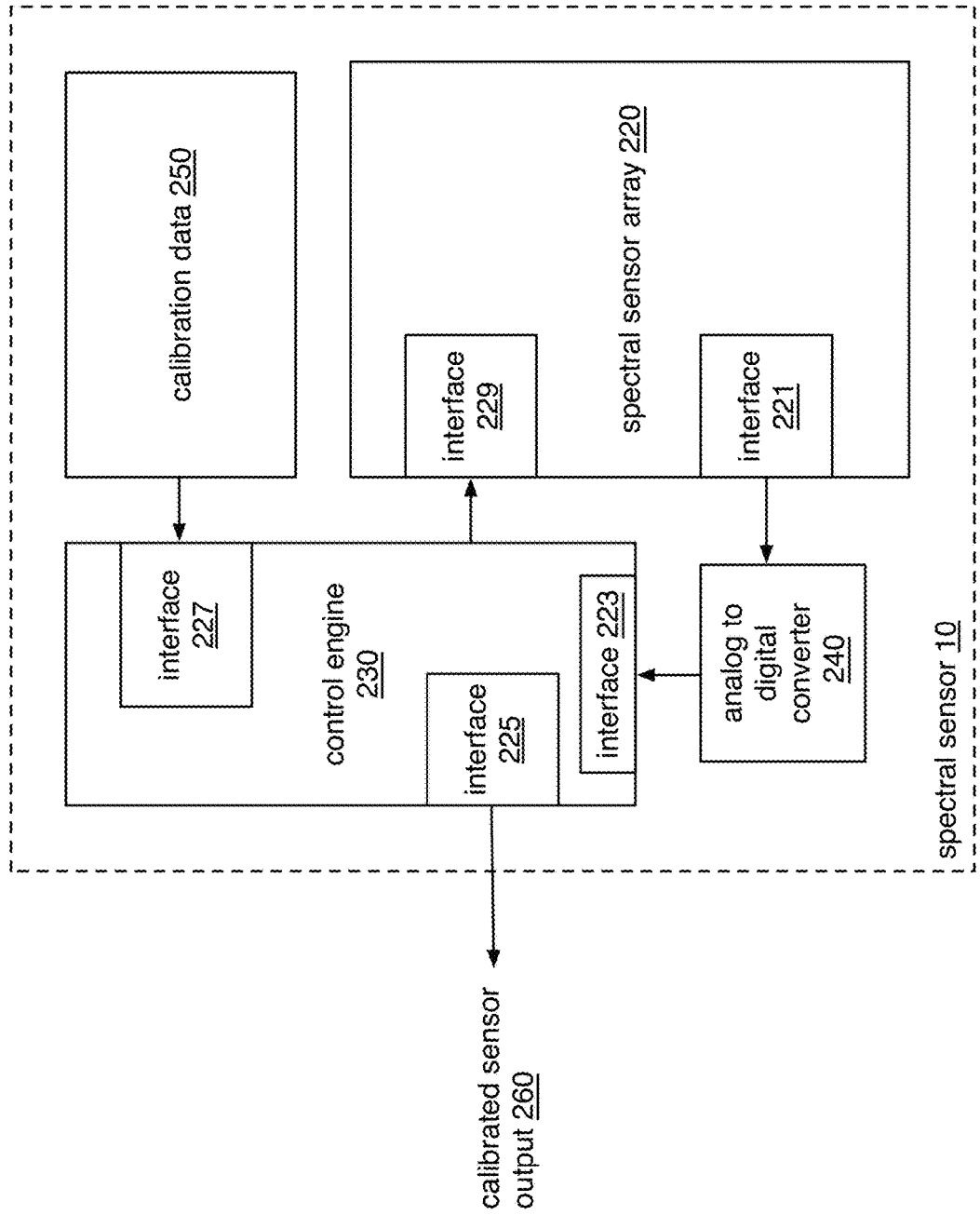

FIG. 4 is a schematic block diagram of an embodiment of a spectral sensor 10 that includes spectral sensor array 220, analog to digital converter (ADC) 240, a control engine 230 and calibration data 250. Spectral sensor 10 can be configured as a single integrated circuit, multi-chip module, as a chip set, or as included elements embodied in a single integrated circuit. In an example, spectral sensor array 220 is calibrated during the manufacturing and/or testing process of spectral sensor array 220, in order to correct for variance inherent to manufacturing processes, such as inter-die variation between sensors, as well as intra-die variance. In an example, the calibration data is stored in memory (such as flash memory) included in spectral sensor 10, or on memory included on the same integrated circuit as spectral sensor array 220.

In an embodiment, the analog output of spectral sensor array 220 is converted by analog to digital converter (ADC) 240 for input to control engine 230. In an example, calibration data collected during the manufacturing and/or testing of spectral sensor array 220 is stored in memory as calibration data 250 and control engine 230 uses calibration data 250 to "correct" the output received from ADC 240. In another example calibration data 250 can also be collected and/or amended heuristically from implementation of spectral sensor 10. In yet another example, calibration data 250 may be collected and/or amended during manufacture, testing or use of a user device in which spectral sensor 10 is enabled.

In yet another example, the spectral sensor consists of a plurality of single photon detectors, such as Single Photon Avalanche Diodes (SPADS) or other Micro Photon Devices configured in a spectral sensing array or pseudo array. The digital information from the resultant spectral sensing array can then be directly input to the control engine 230. The examples of SPADS include, but are not limited to Single Pixel Silicon, InGaAs detectors and bidimensional arrays of CMOS detectors.

In the example of FIG. 4, calibration data 250, as discussed above with regard to FIG. 3, is used to correct the output of spectral sensor array 220 over a variety of input/operating conditions. In the example, control engine 230 provides a calibrated sensor output from the spectral sensor array 220 using calibration data 250. Calibrating the output of spectral sensor array 220 in this manner involves a mathematical correction that requires a matrix requiring comparatively complex mathematics. For example, a matrix inversion may be used to construct a correction matrix for the example, however the resultant correction matrix would likely be relatively imperfect while also being exceedingly complex to develop and/or execute.

FIG. 5A provides a schematic block diagram of an embodiment of a spectral sensor 10, wherein hardware and/or software capable of providing artificial neural network functions, labeled as artificial neural network 370, is included in spectral sensor 10. In an example, the artificial neural network 370 is included in a spectral sensor 10 in a module or integrated with one or more elements of spectral sensor 10 and is configured to provide a corrected output based on a corrected output from artificial neural network 370. In an example, calibration data 350 can be provided directly to artificial neural network 370. In another example, calibration data 350 can be used by the control engine 230 illustrated in FIG. 4 to provide a calibrated output from sensor array 320 to artificial neural network 370.

In another example, artificial neural network 370 is implemented by an external computing device. In another example, the artificial neural network 370 is implemented in another physical layer or element of a 'stacked sensor' using 3D integration methods. In an example, the artificial neural network can be connected in a massively parallel fashion to the spectral sensor by 3D Stacking. As an example, each pixel or filter patch can be configured to include a direct connection to one or more artificial neural network nodes.

Artificial neural network 370 comprises an interconnected structure of "artificial neurons" that function as a pathway for data transfer. A conventional computing system can be made up of a number of simple, highly interconnected processing elements that process information to external inputs with their dynamic state response. In contrast, a neuron, in the context of artificial neural network 370, is able to produce a linear or a non-linear response. In an example, a non-linear artificial network is made by the interconnection of non-linear neurons; such a non-linear system can comprise inputs that will not be proportional to outputs.

In an example, artificial neural network 370 is "loaded" with weights or coefficients derived from a training process, such as that illustrated in FIG. 8B and described in associated text. The coefficients can be loaded directly into artificial neural network 370, or stored with calibration data 350 for input into artificial neural network 370.

Figure 5B:
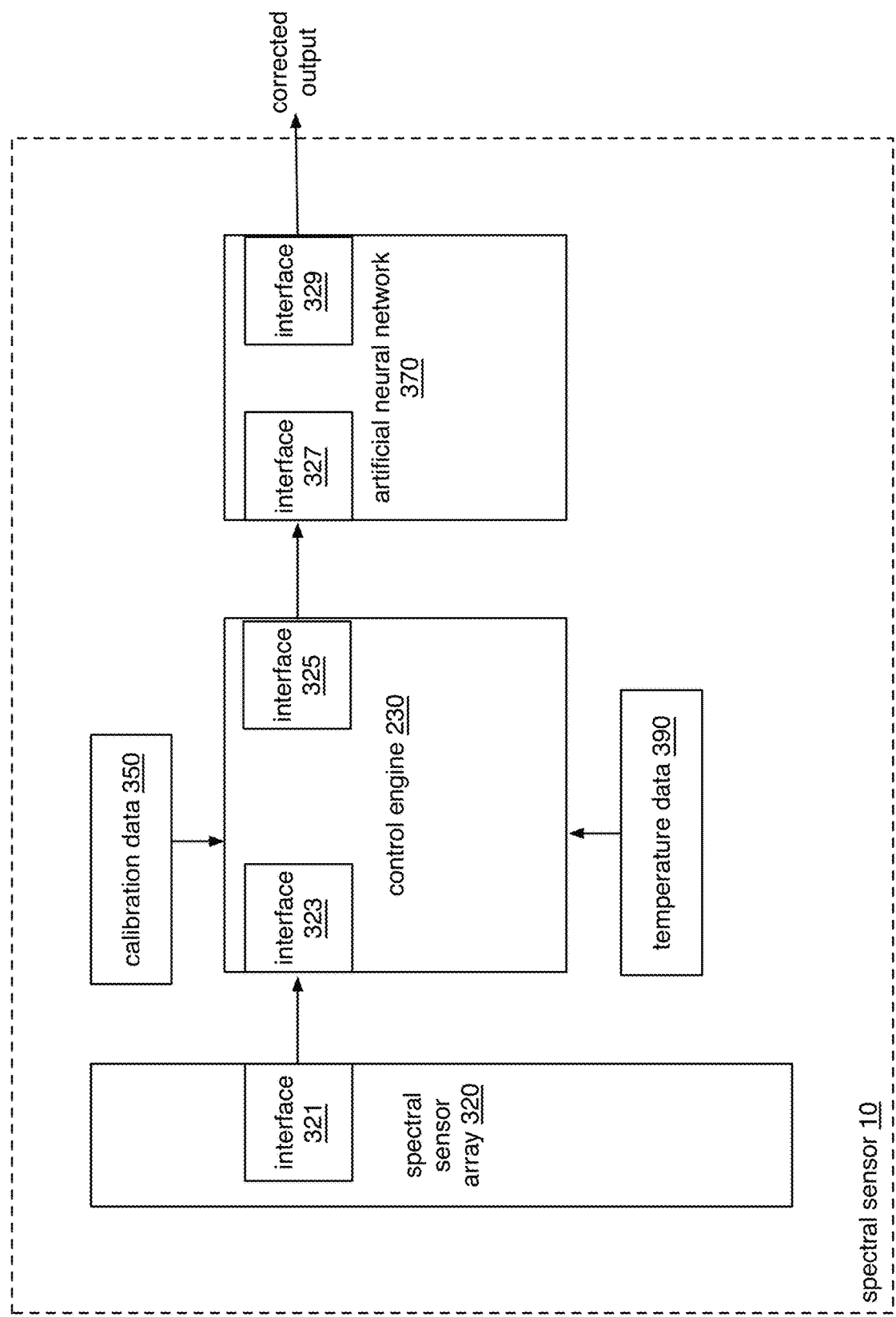

FIG. 5B provides a schematic block diagram of an embodiment of a spectral sensor 10, wherein an artificial neural network is provided temperature data to improve accuracy and/or precision of a corrected output. In an embodiment, temperature data 390 is provided to the artificial neural network 370. In an example, temperature data 390 is collected from a temperature sensing device external to the spectral sensor 10 and can be transmitted to the sensor array continuously or intermittently using a duty cycle, where the temperature signal is active for only a fraction of a given period of time. Temperature data 390 can also be provided to artificial neural network 370 continuously or using a duty cycle.

Temperature data 390 can be stored in dedicated memory or in memory shared with other spectral sensor elements. In an example, temperature data 390 is stored as numerical values representative of actual temperature, such as a voltage or resistance value. In another example, temperature data 390 is converted to a temperature value before it is transmitted to artificial neural network 370.

Figure 6A:
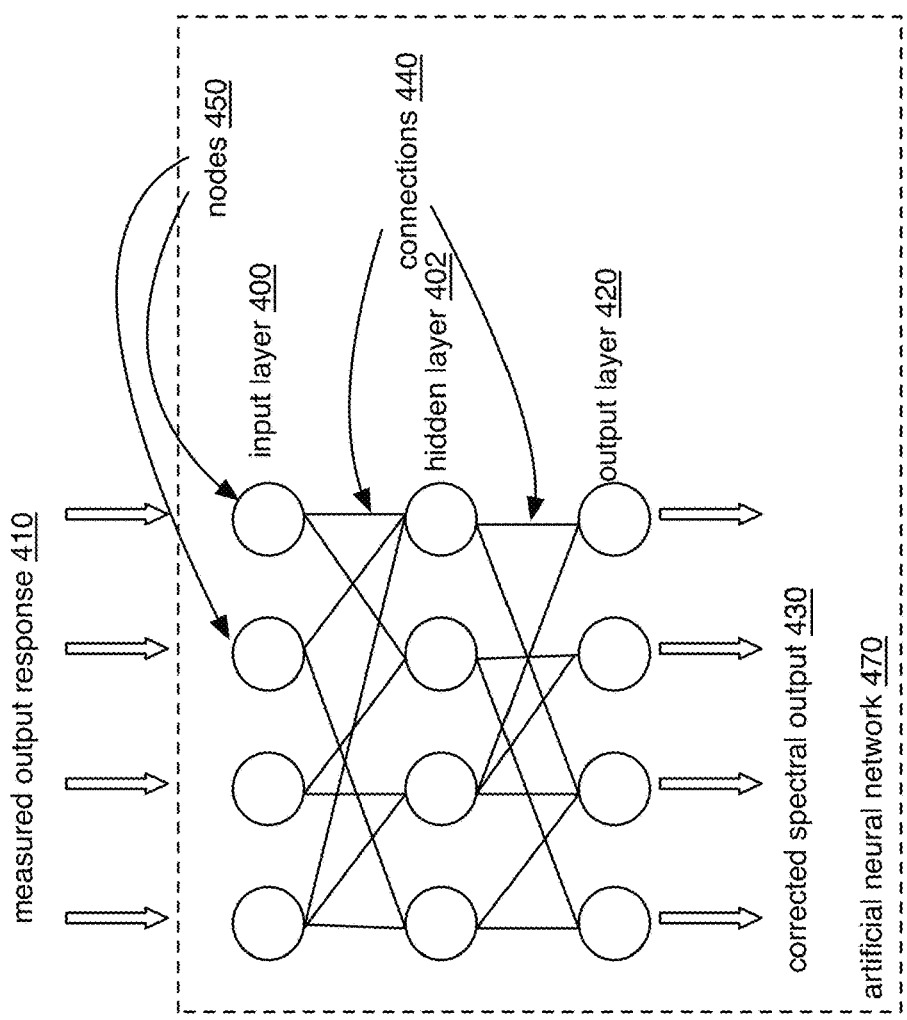

FIG. 6A provides a simplified illustration of an artificial neural network, such as artificial neural network 370, in the context of a spectral sensor, such as spectral sensor 10. In the example, a measured output response 410, such as the calibrated sensor output 260 referred to in FIG. 4, is input to an input layer 400 of artificial neural network 470, with input layer 400 including artificial neurons (nodes) 450 interconnected to one or more hidden layer 402 nodes and an output layer 420 of nodes. In another example, there is no hidden layer 402, with input layer 400 nodes being interconnected to output layer nodes without a hidden layer of nodes. In yet another example, of what we will call a single-layer neural network, the inputs to artificial neural network 470 are fed directly to output layer nodes using a series of weights, where the sum of the products of the weights and the inputs is calculated in each node, and if the value is above some threshold (typically 0) the neuron fires and takes the activated value (typically 1); otherwise it takes the deactivated value (typically −1).

Figure 6B:
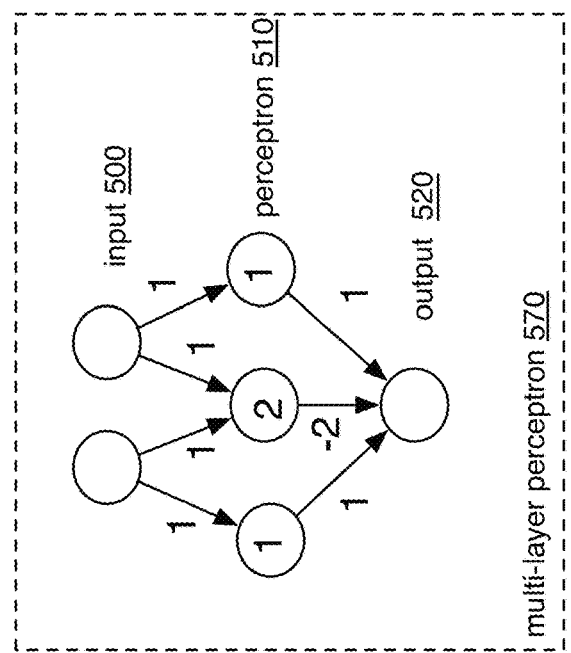

FIG. 6B provides a simplified illustration of an artificial neural network sometimes called a multi-layer perceptron, where each node in one layer has directed connections to the nodes of the subsequent layer, where multiple layers of computational units are interconnected in a feed-forward arrangement. For example, if a value within the perceptron nodes 510 (nodes) represent each node's explicit threshold (which can be factored out so that all nodes have the same threshold values that annotate arrows represent the weight of the inputs. This net assumes that if the threshold is not reached, zero (not −1) is output. Accordingly, in the example, a two-layer neural network is capable of calculating XOR.

In a simplified example, an input 500 is provided to the neural network and a required target response is set at the output 520 and from the difference of the desired response along with the output of real system an error is obtained. The error information is fed back to the system and it makes many adjustments to their parameters in a systematic order. After repeating this process for a sufficiently large number of training cycles, the network can converge to a state where the error of the calculations is small and the network has "learned". In an example, a general method for non-linear optimization is applied, where the network calculates the derivative of the error function with respect to the network coefficients or weights and changes the coefficients such that the error decreases.

Various forms of neural networks can be used to provide spectral correction, including, but not limited to, feedback artificial neural networks, feed-forward artificial neural networks, classification-prediction artificial neural networks and others.

FIG. 7A is a logic diagram illustrating an example method for training an artificial neural network to provide corrected spectra. In step 600 spectral output is collected from a sensor array, such as sensor array 220, across a range of input power and wavelengths, such as illustrated in the table associated with FIG. 7A. In an example, a sweep of monochromatic light across a desired wavelength range can be presented to the sensor array while input power is fixed; input power can then be increased incrementally and swept for the desired wavelength range at each desired input power setting. In an alternative example, input power can be increased in fixed steps for each fixed wavelength of a desired wavelength range. In yet another alternative example, select wavelength and input power pairs, such as those shown in the chart from FIG. 7A, can be selected statistically or randomly (or pseudo randomly) to fill out a matrix. In another example a matrix, such as the matrix illustrated in FIG. 7A, can be modified using a fractional factorial design to reduce training runs and resources.

In the example of FIG. 7A, light wavelengths and input power are considered. In other examples, input factors can be many and varied. Example input factors can include, for example, a signal or other indication of a type of illumination source (such as laser, natural light, light-emitting diode (LED) light, etc.), a type of object being sampled (such as human skin, outdoor scene, etc.) and/or an intended use for the spectral output (such as health analytics, white balancing, etc.). See FIG. 8D and accompanying text for additional input factors. In an example, multidimensional matrices can be used to accommodate a plurality of input factors. In a related example, multidimensional matrices designed to accommodate multiple input factors can utilize full and fractional factorial designs.

The example, the matrix of FIG. 7A includes monochromatic light at wavelengths from 720 nm to xxx nm in 10 nm increments for each of 1-y input power units. In practice wavelengths could be incremented in smaller increments, such as 1 nm, or in increments >10 nm and input power can be incremented in a like manner.

The method of FIG. 7A results in a characterization model of a hypothetical spectrometer M with dimensions L×S×N, where L is the number (#) of input power increments, S is the # of wavelength increments and N is the number of filter "patches". A filter patch, in the example, is the number of filter elements across the sensor array that select for the same wavelength transmission. In an example, this spectrometer "model" can provide full-resolution spectra (single wavelength increments of monochromatic light) and output N values. For example, for a 64-channel spectrometer there would be 64 outputs. The method begins at step 600, with an output being collected for a plurality of input power and wavelength pairs and continues at step 610, where a large number of synthetic input spectra are created. In a specific example, 100 million spectra, covering substantially all conceivable permutations that the spectrometer could be exposed to. In another specific example, the synthetic input spectra can be selected for targeted permutations of spectrum exposure conditions. These synthetic input spectra can then be used to train for a corrected spectrum, as discussed above.

In step 620 the artificial neural network is trained (i.e. the coefficients or weights of the neural network are determined) so that when synthetic spectra are provided to the spectrometer the artificial neural network outputs the artificial spectra (i.e. error in the spectrometer is minimized to an acceptable amount). In step 630 the coefficients, or weights are loaded into the artificial neural network (such as artificial neural network 370 of FIG. 5). The spectrometer is then enabled to correct any input light to the spectral array to produce a corrected spectrum.

FIG. 7B is a logic diagram illustrating an example method for adaptively correcting the spectral output from a sensor array. The method begins at step 640, with the sampled spectrum from an object or scene being recorded. In an example, the recording can include one or more of saving the sampled spectrum in memory, holding the sampled spectrum in a buffer and providing readouts as received to a processing module. The method continues at step 642, with the recorded spectrum being analyzed. In an example, the analysis can include analyzing the recorded spectrum to determine one or more of intensity at select wavelengths, total energy, ratios for recorded peaks in the spectrum (such as peak/valley ratios, or ratios between peaks), relative smoothness or relative spikiness signal, etc.).

At step 644 the method continues with a calibration method being determined based on the analyzed spectrum and one or more additional input factors. Additional input factors can include, for example, a signal or other indication of a type of illumination source (such as laser, natural light, light-emitting diode (LED) light, etc.), a type of object being sampled (such as human skin, outdoor scene, etc.) and/or an intended use for the spectral output (such as health analytics, white balancing, etc.). See FIG. 8D and accompanying text for additional input factors. In an example, the calibration method can include a matrix, such as the matrix illustrated in FIG. 7A. Other calibration methods include one or more of calibrating using one or more of two wavelengths (such as two wavelengths useful for peripheral oxygen saturation ($SpO_2$) measurement), calibrating using principal component analysis and calibrating using other schemes. At step 644 the determined calibration method is applied to the sampled spectrum. At step 648, when the correction is complete the corrected sampled spectrum is analyzed to determine whether it is within predetermined limits and when the corrected sampled spectrum is not within predetermined limits step 642 can be repeated and/or a different calibration can be used until the corrected sampled spectrum is within predetermined limits. In an example, the predetermined limits can be based on one or more input factors such as one or more of meta-data associated with an object or scene, a classification limit, a lookup table, a formula or a calibration method utilized.

FIG. 7C provides logic diagram illustrating another example method for adaptively correcting the spectral output from a sensor array. The method begins at step 650, with an optical sensor array associated with the spectral sensor system receiving light of N input powers for each wavelength of light of M wavelengths of light, to produce N×M wavelength and input power pairs. In an example, each wavelength of light of the M wavelengths of light and each input power of light of the N input powers of light is received by the optical sensor array in a predetermined sequence. In another example, each optical sensor of the optical sensor array is associated with an optical filter of a plurality of sets of optical filters and each optical filter of a set of optical filters is configured to pass light in a different wavelength range. The method continues at step 652 with the spectral sensor system generating a plurality of signals to produce a generated signal for each wavelength and input power pair, where each of the plurality of signals is representative of the received light at each wavelength and input power pair of the N×M wavelength and input power pairs. At step 654, the spectral sensor system determines a plurality of error coefficients, with each error coefficient of the plurality of error coefficients being representative of the difference between a generated signal and a target value for a wavelength and input power pair. At step 656 the sensor system uses the plurality of error coefficients to train an artificial neural network configured to adjust a spectral response generated by the optical sensor array and at step 658 the output from the trained artificial neural network can be used to adjust the spectral response generated by another optical sensor array.

In a specific example of implementation, the artificial neural network referred to in FIG. 7C can be configured to receive information associated with a scene being sampled by another spectral sensor. In yet another example, the output from the trained artificial neural network is provided to another artificial neural network that is associated with another optical sensor array (in another spectral sensor system), where the other artificial neural network is configured to receive information associated with a scene being sampled by the other spectral sensor system.

In an example, the artificial neural network referred to in FIG. 7C can be trained with coefficients for N×M wavelength and input power pairs, along with corrections based on other input factors, such as the input factors referred to with reference to FIG. 7A. In another example, a trained artificial neural network can be used to provide weighting for one or more artificial neural networks associated with other spectral sensor systems, which can themselves be trained based on various input factors.

FIG. 8A provides an illustration of an example spectral sensor where input parameters 310, such as a sweeping of monochromatic light over selected wavelengths at select input power units are provided at spectral sensor 10 and an uncorrected output response 500 is collected (such as L×S×N from step 600 of FIG. 7A). In an example, a spectral sensor 10 includes calibration data collected during testing and/or manufacture of spectral sensor 10, where the calibration data are specific to the spectral array 220 of spectral sensor 10. In an example, the calibration data is stored in flash memory associated with spectral sensor 10.

In the example, the uncorrected output response 500 is a measure of how the spectral sensor 10 behaves when it is swept with monochromatic light at incremental input power levels. In an "ideal" spectral sensor each sensor or pixel, in combination with an associated filter element produces a signal that is a substantially perfect representation of the input power and light provided at the spectral sensor 10, such that a linear sequence of wavelengths at a given input power results in a spectral output response that substantially matches the input power and light provided at the spectral sensor 10 (i.e. the spectral output response would be "ideal"). Since no spectral sensor operates in such an ideal manner, the uncorrected output response 500 will deviate from the ideal spectral output response and will require correction to accurately represent the input parameters 310.

In FIG. 8B provides an illustration of an example spectral sensor utilizing an artificial neural network. In an example, raw spectral data, such as the uncorrected output response 500 from FIG. 8A, is used to create spectrometer model 510 for spectral sensor 10, such that spectrometer model 510 reflects the non-ideality of spectral sensor 10 for all of the input parameters 310 provided to spectral sensor 10, such as in the example of FIG. 8A.

In the example, artificial spectra 560 are received at spectrometer model 510, the output of which is then input to an artificial neural network, such as artificial neural network 370 and compared to a desired or expected spectral output for artificial spectra 560. In an example, error 530 is repeatedly determined for the artificial spectra 560 and input to artificial neural network 370 to generate coefficients that reflect the difference between the artificial spectra 560 and spectrometer model 510. The generated coefficients can then be stored and subsequently loaded into a generic artificial neural network to correct the spectrum in an associated spectral sensor. In an example, a number of artificial spectra 560 is determined based on the desired precision and accuracy for spectral sensor 10 and can, for example, exceed 100 million spectra.

In an embodiment, the spectral sensor 10 can provide filter patterns across the spatial areas of a sensor array (such as spectral sensor array 100 from FIG. 1) in order to optimize a corrected spectral output response 520. For example, the pattern of filters across the spectral sensor array (such as spectral sensor array 100 from FIG. 1) can be scrambled, and/or repeated multiple times across the spectral array. The repeated patterns, for example, can reduce shading effects and other effects from non-uniformity that can be the result of other elements associated with the spectral sensor 10, such as for example, collimating optics.

In another embodiment, the effect of changes to illumination and/or scene tilt can be remedied and or altered by the artificial neural network 370. Scene tilt can be described as the relationship between a scene or object on a vertical and/or horizontal axis relative to an imager, such as a spectral imager. For example, a scene that is relatively perpendicular in a vertical and horizontal axis to the sight-line of an imaging system (such as a camera) could be described as having zero degrees (0 degrees) of tilt. If the sight-line is described as a line extending from an imager's viewpoint to a sampled object or area (such as a stage) then a tilt of 20 degrees could indicate that the sampled object deviates by 20 degrees from perpendicular to the sight-line.

In an example, synthetic spectra, such as artificial spectra 560, includes measured parameters for various increments of tilt and illumination that can be used in training to minimize the effects of these parameters. In an example, the correction of tilt and or illumination can lower the requirement for collimating elements in the sensor array. In a specific example, measured parameters such as a scene tilt or illumination change could be used with an artificial neural network 370 configured to allow a user to impose an effect on an image, such as scene tilt. In an example, a tilt-shift effect could be provided, such that an image with 0 degrees of tilt could reflect a variable amount of tilt to provide a tilt-shift effect. In a specific related example, a measured scene tilt could be used with an artificial neural network 370 to allow a user to manipulate the focal plane of an image to correct distortion due to tilt. In another specific related example, a measured scene tilt could be used with an artificial neural network 370 to allow a user to manipulate the focal plane of an image to attenuate the convergence of vertical and/or horizontal lines of one more features in the image.

In yet another embodiment, the effect of changes to ambient light and/or temperature changes can be remedied by the artificial neural network 370. In an example, the synthetic spectra, such as artificial spectra 560, includes measured parameters for various ambient light conditions and temperatures that can be used in training to minimize the effects of these parameters.

In a specific example of implementation and operation, a spectral sensor system includes a plurality of optical sensors arranged on an integrated circuit, where the plurality of optical sensors are arranged in an array and an interface between the plurality of optical sensors and a first processing device configured to transmit information between each other. In an example, a plurality of sets of optical filters are configured as a layer located atop the plurality of optical sensors, where a set of optical filters of the plurality of sets of optical filters includes a plurality of optical filters and each optical filter of the plurality of optical filters is configured to pass light in a different wavelength range. In the example, a memory configured to interface and communicate with the first processing device and store calibration data associated with the plurality of sets of optical sensors is included, with a second processing device comprising an artificial neural network configured to correct a spectral response generated by the plurality of optical sensors, along with an interface between the first processing device and the second processing device.

FIG. 8C illustrates an example spectral sensor where a physical scene 160 is provided to a spectral sensor 10, which is then output to a trained artificial neural network 370 to provide a corrected spectral output response 520 for physical scene 560. FIG. 8D illustrates an example spectral sensor where meta-data of a physical scene is provided to the artificial neural network, such as artificial neural network 370. In an example, physical scene meta-data 570 is predetermined for use by artificial neural network 370. In an example, if a particular plant is the subject of analysis, known spectral responses for that plant can be used to increase the efficiency of artificial neural network 370. This could be accomplished by one or more of optimizing the measurement range, increasing the granularity of measurements in a portion of the physical scene, or otherwise manipulating the analysis based on the meta-data 570. Physical scene meta-data 570 can include, but is not limited to, data provided by additional sensors such as gyroscopes, magnetometers, accelerometers, temperature sensors and image sensors.

In a specific example of implementation and operation, the meta-data 570 can include information about a physical scene 560 that the artificial neural network 370 either cannot correct or would produce a corrected spectral output response 520 outside of acceptable limits. In an example, the artificial neural network 370 can be configured to provide a notification, such as a signal, indicating that a correction is not within acceptable limits. In another example, the artificial neural network 370 can be configured to provide a notification, such as a signal, indicating that a correction is within acceptable limits, effectively informing a user that the corrected spectral output response 520 can be trusted. Examples of meta-data 570 information that artificial neural network 370 either cannot correct or would be outside of acceptable limits include one or more of too low input light, sensor saturation, or the angle of incidence for incoming light too to be corrected by the artificial neural network 370.

In another specific example of implementation and operation, the artificial neural network 370 can be configured with a plurality of operational modes. In an example, the artificial neural network 370 can be configured with a high accuracy-higher power mode that produces a relatively high-quality spectral output but has relatively higher power consumption, or the artificial neural network 370 can be configured with a lower accuracy-lower power mode, where fewer calculations are done to reduce power consumption on a relative basis. In another specific example of implementation and operation, can be configured for a reduced complexity operation to correct for one or more scenarios. For example, the artificial neural network 370 can be configured to select a condition or set of conditions, such as medium light intensity and angle of incidence for incoming light collimated at an angle of 6 degrees before correction is executed by the artificial neural network 370. In an example, the reduced set of conditions can provide, for example, reduced power consumption. Ina related example, a specific correction and be provided by an artificial neural network 370 for use in a non-neural based processor in order to reduce the relative power or cost for spectrum correction.

In another specific example of implementation and operation, the artificial neural network 370 can be configured to provide a confidence or accuracy value with a corrected spectral output response 520. For example, if a red patch (or tile) is measured at 50% input power the resultant corrected spectral output response 520 for the measurement will include an absolute/relative accuracy of 1% at the 700 nm wavelength and an absolute/relative accuracy of 5% at 500 nm. In an example, a confidence value could be used in a subsequent application layer, such as a subsequent software layer, to scale the "importance" of the corrected spectral output response 520 or portions thereof at certain wavelengths with the confidence values. In an example, if the corrected spectral output response 520 between 500 nm and 550 nm has a relatively low confidence value, to be accurate, then the subsequent application layer could assign lower importance to that portion of the corrected spectrum.

In an example, a neural network correction algorithm can include one or more weighted loss functions (sometimes called weighted cost functions) associated with an area and/or range of interest, such as a portion of physical scene 560 or one or more identified objects or areas from the physical scene 560. In an example, a weighted loss function can be used to increase the sensitivity of a spectral sensing system, such as spectral sensor 10 to a specific area and/or range being sampled. In a specific example of implementation and operation, one or more weighted loss functions can enable spectral sensor system hardware (such as spectral sensor 10) to be adaptable for use in fields with disparate requirements and performance expectation. In an example, the one or more weighted loss functions are fixed at manufacture. In another example, the one or more weighted loss functions are selectable manually. In yet another example, the one or more weighted loss functions are determined based on an algorithm, such as a pattern recognition algorithm.

In a specific related example, the measurement of hydration, such as the hydration level in skin, can be implemented using data from spatially separated areas of a sensor, in order to increase the accuracy and/or precision at 5 particular portions of the spectrum used for hydration analysis. In the example, spectrum accuracy and/or precision may relatively less relevant in other spectral ranges, thus the spectral sensor system can reduce or eliminate the samples from those spectral ranges.

In another example, spectral sensor 10, in combination with artificial neural network 370 can be used to generate a confidence image, where the confidence image provides information sufficient to determine whether the actual measured spectrum is appropriate. For example, artificial neural network 370 can provide an indication of the deviation of the measured spectrum from training data already determined. The deviation can then be used to indicate abnormal spectra, (spectra that cannot normally occur) indicating a false measurement.

In another example the spectral sensor, in combination with artificial neural network 370, can be configured to provide spectral response correction as an intermediate step, before a corrected spectrum is output. In the example, an artificial neural network corrected spectral response is passed to subsequent layer and an algorithm or the artificial neural network is used to determine a property or properties derived from the measured spectrum. For example, a property such as water content and/or oxygen content in a medium being analyzed may be determined, where the determination is based on the corrected spectral response provided by the artificial neural network, without requiring a corrected spectrum.

In one embodiment, physical scene meta-data 570 and/or other data being input to artificial neural network 370 is provided in substantially real time (live), such that artificial neural network 370 is able to constantly revise the corrected output. In another embodiment physical scene meta-data 570 and/or other data is previously stored and provided artificial neural network 370 as required and/or feasible.

FIG. 9 provides an illustration of the relative spectral power distributions for three hypothetical illuminants A, B & C across a visible spectrum. In the example of FIG. 9, the spectrum is provided from 380 nm to 750 nm, however, in some examples, the spectrum could extend below 380 nm and above 750 nm, with the relative spectral power distributions for the A, B & C illuminants extending below 380 nm and above 750 nm as well. In an example, an illuminant can be represented as a theoretical "standard illuminant" to provide a baseline for comparing images collected on various imaging devices under different lighting characteristics. Accordingly, a standard illuminant can be regarded as an "ideal" reference for determining the accuracy of a given imager used to image a scene or object in different imaging environments. In an example, comparing the imager output of a scene or object collected by a given imager to the standard illuminant across a desired spectrum can provide a spectral power distribution differential between the collected imager output and the hypothetical standard illuminant.

In a specific example referring to FIG. 9, the standard illuminant for an imager with the three illuminants A, B & C, is a theoretical spectral power distribution within a defined lighting environment. For example, the International Commission on Illumination (CIE) defines a standard illuminant A as intending to represent typical, domestic, tungsten-filament lighting, while a standard illuminant B can be representative of noon sunlight, while a standard illuminant C can represent average day light. In practice, the ideal reference provided for with a standard illuminant can be almost any baseline useful for providing an ideal expected result. Accordingly, the standard illuminant can be described in a variety of mechanisms, limited only by an agreement as to what the ideal expected result is (or should be).

Referring again to FIG. 9, in a specific example of operation an imager output that is not corrected for illuminant can provide imperfect information when the imager output is to be used for applications requiring accurate spectral power information over a desired spectrum. Examples requiring relatively accurate spectral power information include, but are not limited to, health related applications, such as detection of skin types and skin anomalies, agricultural applications, remote monitoring applications and others. Additional examples include consumer applications, for example the use of mobile imaging devices, such as smart phones and smart watches, to analyze cosmetics, hydration, sun exposure and the like. Even traditional imaging applications can be negatively affected when illuminant inaccuracies are not corrected. The spectral characteristics of areas imaged can include information useful for a myriad of applications that can themselves depend on a baseline comparison to a spectral power distribution reference.

Referring to FIG. 8C, a corrected spectral output response 520 is determined for physical scene 560. Referring to FIG. 3, in an example, the corrected spectral output response 520 of FIG. 8C can represent the corrected spectrum 190 for the raw spectrum output 192 of a hypothetical spectral sensor 10. In an example, the corrected spectrum 190 reflects corrections to the raw spectrum output 192 due to differences between the output of a hypothetical spectral sensor 10 and the output of an "ideal sensor" used to image the same scene or object. Accordingly, the calibration of hypothetical spectral sensor 10 provides for a corrected output for hypothetical spectral sensor 10, however, a corrected output alone might not provide the spectral power distribution differential from a standard illuminant response as discussed with respect to FIG. 9.

FIG. 10 provides a top-down illustration of a filter array with filters provisioned in a 3×3 patterns of 9 spectral bands each across an imager array. In the example, Fabry-Pérot filters with different center wavelengths are patterned across the spectral sensor as a mosaic structure repeated across the array. In other embodiments, the 3×3 filter pattern can be replaced with other patterns, such as a 2×2 pattern, a 4×4 filter pattern, a 5×5 filter pattern or a 3×4 pattern, etc., as dictated by resolution and/or manufacturing requirements. In an example, a 3×3 pattern of filters provides 9 different cavity thicknesses, which are then repeated across an example sensor array. In the example of FIG. 10 each of the 9 filter thicknesses (illustrated as filters 20A-20H, etc.) is repeated 12 times across the 12×9 array of optical pixels on filter array 712.

In a sensor system based on FIG. 10, optical pixels for an image sensor (such as optical sensor 10 illustrated in FIG. 1A) are disposed on an integrated circuit with a plurality of sets of interference filters manufactured on top of the optical pixels. In an example, a set of nine (9) interference filters 20A-20I are arranged in a mosaic pattern, each of which is configured to pass light in a different wavelength range. In an example, each set of interference filters is aligned to at least a set of optical sensors, such that each set of optical sensors can sense a localized bandpass response with 9 channels. The set of optical sensors and filter arrangement are then repeated across the array, enabling the optical sensor array to provide multiple measured light spectra spatially separated across different areas of an image sensor. As used herein, an individual optical sensor corresponds to a pixel (pixel=smallest addressable element), where a pixel is a photodiode. Accordingly, "optical sensor", "optical pixel" and "pixel" are used interchangeably.

In an example, an image sensor incorporating the filter array 712 of FIG. 10 can provide light distortion information for different areas of the image sensor, allowing white-balance correction to be extended to each of those areas. In an example of implementation, a sensor system for imaging a scene can comprise a plurality of optical sensors on an integrated circuit, with a plurality of sets of interference filters, such as filter elements 20A-20I of FIG. 1. In the example, each set of interference filters of the plurality of sets of interference filters can include a plurality of interference filters arranged in a pattern, where each interference filter of the plurality of filters is configured to pass light in a different wavelength range. In an example, each set of interference filters of the plurality of interference filters is associated with a spatial area of the scene and a spectral response can thus be determined for each spatial area of the scene.

Referring to FIG. 10, in an example of implementation, a set of interference filters of a plurality of sets of interference filters can be spatially separate from others of the plurality of sets of interference filters and in another example, each set of interference filters of the plurality of sets of interference filters can spaced randomly between a plurality of optical sensors associated with filter array 712.

FIG. 11A illustrates an example imager system where a physical scene 690 is provided to a spectral sensor 780, which is then output to a calibration processor 710, the output of which is then output to trained artificial neural network 770 to provide an illuminant output response 720 for physical scene 690. FIG. 11B illustrates an example spectral sensor where calibrated spectral response data is provided to train an artificial neural network, such as artificial neural network 770.

In an example, a neural network correction algorithm can include one or more weighted loss functions (sometimes called weighted cost functions) associated with an area and/or range of interest, such as a portion of physical scene 690 or one or more identified objects or areas from the physical scene 690. In an example, a weighted loss function can be used to increase the sensitivity of a spectral sensing system, such as spectral sensor 780 to a specific area and/or range being sampled. In a specific example of implementation and operation, one or more weighted loss functions can enable spectral sensor system hardware (such as spectral sensor 780) to be adaptable for use in fields with disparate requirements and performance expectations. In an example, the one or more weighted loss functions are fixed at manufacture. In another example, the one or more weighted loss functions are selectable manually. In yet another example, the one or more weighted loss functions are determined based on an algorithm, such as a pattern recognition algorithm.

FIG. 11C provides a schematic block diagram of an embodiment of an imager system 800 comprising a spectral sensor array 820, a calibration processor 830 and artificial neural network 870. In an example, spectral sensor array 820 comprises a plurality of sets of optical sensors, with each optical sensor set adapted to collect a range of spectral responses for a spatial area of an image and transmit the collected responses using interface 821 to calibration processor 830, which receives the collected responses via interface 825. In an example, calibration processor 830 uses calibration data 850 to "correct" the collected responses to produce a corrected spectrum for each set of optical sensors and transmits the corrected spectrum for each set of optical sensors to trained artificial neural network 870 via interface 825. Artificial neural network 870 receives the corrected spectra via interface 827 and processes the corrected spectra to produce an illuminant corrected spectra for each set of optical sensors and outputs the illuminant corrected spectra via interface 829 as illuminant corrected response 720.

FIG. 12 is a logic diagram illustrating a method for producing illuminant corrected spectra for an array of optical sensors. At step 940 a calibration processor receives spectral response data from plurality of sets of optical sensors and at step 942 the calibration processor calibrates the spectral response for each set of optical sensors to produce a calibrated spectrum for each set of optical sensors. At step 944 an artificial intelligence engine is used to classify, via an artificial intelligence model, the calibrated spectrum for each set of optical sensors to provide a corrected illuminant for each set at step 946. Finally, at step 948, the artificial intelligence engine outputs the calibrated and illuminant corrected response for each set of optical sensors.

In a specific example of implementation and operation, a sensor system comprises a plurality of optical sensors arranged on an integrated circuit, wherein the plurality of optical sensors are arranged in an array, a plurality of sets of optical filters configured as a layer located atop the plurality of optical sensors, wherein a set of optical filters of the plurality of sets of optical filters includes a plurality of optical filters, wherein each optical filter of the plurality of optical filters is configured to pass light in a different wavelength range.

In an example, a first processing device is configured to determine a spectral response associated to each set of optical filters, an interface is provided between the plurality of optical sensors and a first processing device configured to transmit information therebetween and a second processing device is provided comprising an artificial neural network configured to determine an illuminant spectrum associated to each spectral response and an interface is provided between the first processing device and the second processing device that is configured to transmit information there between.

In a specific example, the artificial neural network is configured to decouple the illuminant spectrum from a spectral response associated to a set of optical filters. In another specific example, the first processing device is configured to return an illuminant-independent spectrum for each spectral response. In another specific example, each set of optical filters is associated with a section of a scene. In yet another specific example, each part of a scene being imaged comprises an area of skin, wherein the first processing device is configured to return an illuminant-independent skin spectrum. In a related example, the illuminant-independent skin spectrum is used to extract skin biomarkers and in a related example, the skin biomarkers includes information relate to one or more of melanin, hemoglobin, oxygenation hydration.

In a specific example, a color image sensor comprises an array of pixels, where a subarray of pixels is configured to capture an image of a section of a scene, where the section of a scene is associated with a set of optical filters and an interface between the color image sensor and the first processing device is configured to transmit information there between. In another specific example, the first processing unit is configured to return a corrected color output of each subarray of pixels of the color image sensor. In yet another specific example, the artificial neural network is configured to correct the color output of each subarray of pixels of the color image sensor. In yet another related specific example, the corrected color output of each subarray of pixels is illuminant-independent. In another specific example, the corrected color output for each subarray of pixels is neutralized by a neutral illuminant spectral profile. In an example, a neutral illuminant spectral profile can be based on standard illuminants, (referring again to FIG. 9) or any other mutually understood or otherwise predetermined baseline spectral power distribution. In an example of implementation and operation optical filters in at least some of the sets of the plurality of sets of optical filters are interference filters.

In an example of operation, an example method for execution by one or more sensor systems comprises receiving light, by an optical sensor array associated with the one or more sensor systems, where each optical sensor of the optical sensor array is associated with an optical filter of a plurality of sets of optical filters and each optical filter of a set of optical filters is configured to pass light in a different wavelength range. In an example, the method includes generating a plurality of spectra, wherein each spectrum of the plurality of spectra is associated to each set of optical filters and determining a plurality of error coefficients, where each error coefficient of the plurality of error coefficients is representative of a difference between a generated spectrum and a target spectrum for a set of optical filters. In an example, the method continues by using the plurality of error coefficients to train an artificial neural network, where the artificial neural network is configured to determine an illuminant spectrum associated to each set of optical filters.

In a related specific example, the optical filters in each set of the plurality of sets of optical filters are arranged in a pattern, where the pattern for at least some of the sets of the plurality of sets of optical filters is repeated across the array. In an example, the method continues by decoupling the illuminant spectrum from at least a generated spectrum, returning an illuminant-independent spectrum for each generated spectrum. In another example, each set of optical filters is associated with a section of a scene and in another specific example, part of the scene comprises an area of skin. In an example, the method includes extracting skin biomarkers. In an example, at least some of the optical filters in at least some of the sets of the plurality of sets of optical filters are interference filters.

It is noted that terminologies as may be used herein such as bit stream, stream, signal sequence, etc. (or their equivalents) have been used interchangeably to describe digital information whose content corresponds to any of a number of desired types (e.g., data, video, speech, text, graphics, audio, etc. any of which may generally be referred to as 'data').

As may be used herein, the terms "substantially" and "approximately" provides an industry-accepted tolerance for its corresponding term and/or relativity between items. For some industries, an industry-accepted tolerance is less than one percent and, for other industries, the industry-accepted tolerance is 10 percent or more. Other examples of industry-accepted tolerance range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to".

As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may be used herein, one or more claims may include, in a specific form of this generic form, the phrase "at least one of a, b, and c" or of this generic form "at least one of a, b, or c", with more or less elements than "a", "b", and "c". In either phrasing, the phrases are to be interpreted identically. In particular, "at least one of a, b, and c" is equivalent to "at least one of a, b, or c" and shall mean a, b, and/or c. As an example, it means: "a" only, "b" only, "c" only, "a" and "b", "a" and "c", "b" and "c", and/or "a", "b", and "c".

As may also be used herein, the terms "processing module", "processing circuit", "processor", "processing circuitry", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, processing circuitry and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with one or more other routines. In addition, a flow diagram may include an "end" and/or "continue" indication. The "end" and/or "continue" indications reflect that the steps presented can end as described and shown or optionally be incorporated in or otherwise used in conjunction with one or more other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid-state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A sensor system comprises:
   a plurality of optical sensors on an integrated circuit, wherein the plurality of optical sensors are configured in an array;
   a plurality of sets of optical filters atop at least a portion of the array, wherein each set of optical filters is associated with a set of optical sensors of the plurality of optical sensors, wherein a set of optical filters of the plurality of sets of optical filters includes a plurality of optical filters, wherein each optical filter of the plurality of optical filters is configured to pass light in a different wavelength range;

a first interface configured to interface with the plurality of optical sensors;

first processing circuitry operably coupled to the first interface, wherein the first processing circuitry is configured to execute operational instructions to:

receive an output signal from the plurality of optical sensors, wherein the output signal is representative of received light from the plurality of optical sensors and determine a spectral response for each set of optical sensors associated with a set of optical filters;

a second interface configured to interface with the first processing circuitry;

second processing circuitry operably coupled to the second interface, wherein the second processing circuitry is configured to execute operational instructions to:

determine, based on the spectral response for each set of optical sensors associated with a set of optical filters, an illuminant spectrum for each spectral response and substantially remove the illuminant spectrum from the spectral response.

2. The sensor system of claim 1, wherein the illuminant spectrum is determined via an artificial intelligence model.

3. The sensor system of claim 2, wherein the artificial intelligence model is based on a neural network.

4. The sensor system of claim 1, wherein each set of optical filters is associated with a portion of a scene.

5. The sensor system of claim 4, wherein the scene comprises an area of skin, wherein the second processing circuitry is further configured to execute operational instructions to:

provide an illuminant-independent spectrum for the area of skin.

6. The sensor system of claim 5, wherein the illuminant-independent skin spectrum for the area of skin includes information sufficient to determine one or more skin biomarkers for the area of skin.

7. The sensor system of claim 6, wherein the skin biomarkers includes at least one of:
melanin;
hemoglobin;
oxygenation; and
hydration.

8. The sensor system of claim 1, wherein the plurality of optical sensors comprises an image sensor, wherein some optical sensors of the plurality of optical sensors are configured to capture an image of a portion of a scene, wherein the portion of a scene is associated with a set of optical filters.

9. The sensor system of claim 8, wherein the second processing circuitry is further configured to execute operational instructions to:

correct a color output for the image of a portion of the scene to provide a color corrected output for the image of a portion of the scene.

10. The sensor system of claim 9, wherein the illuminant spectrum is determined via an artificial intelligence model, wherein the artificial intelligence model is based on a neural network, wherein the neural network is configured to substantially remove the illuminant spectrum from the spectral response for the image of the portion of the scene.

11. The sensor system of claim 9, wherein the color corrected output of each subarray is a color output that is based on a neutral illuminant spectral profile.

12. The sensor system of claim 9, wherein the optical filters of at least some of the sets of the plurality of sets of optical filters comprise interference filters.

13. A method for execution by a sensor system, the method comprising:

receiving, by an optical sensor array, incident light radiation associated with a scene, wherein the optical sensor array includes a plurality of optical sensors, wherein an optical sensor of the plurality of optical sensors is associated with an optical filter of a plurality of sets of optical filters and each optical filter of a set of optical filters is configured to pass light in a different wavelength range;

outputting, by the optical sensor array, information representative of the incident light radiation;

generating, based on the information representative of the incident light radiation, by first processing circuitry operably coupled to the optical sensor array, a plurality of spectra, wherein each spectrum of the plurality of spectra is associated with a set of optical filters;

determining, based on the plurality of spectra, by first processing circuitry, a plurality of error coefficients, wherein an error coefficient of the plurality of error coefficients is representative of a difference between a generated spectrum and a target spectrum for a set of optical filters;

training, by second processing circuitry, an artificial neural network based on the plurality of error coefficients;

classifying, by the artificial neural network, the plurality of spectra to produce an illuminant spectrum associated with each set of optical filters.

14. The method of claim 13, wherein the optical filters in each set of the plurality of sets of optical filters are arranged in a mosaic, wherein the mosaic for at least some of the sets of the plurality of sets of optical filters is repeated across the optical sensor array.

15. The method of claim 13, further comprising;
substantially removing, by the second processing circuitry, the illuminant spectrum from at least one spectrum of the plurality of spectra;
generating, by the second processing circuitry, an illuminant-independent spectrum for each generated spectrum.

16. The method of claim 13, wherein each set of optical filters is associated with a portion of a scene being imaged by the sensor system.

17. The method of claim 16, wherein the scene comprises an area of skin.

18. The method of claim 17, further comprising:
determining, based on the illuminant spectrum associated with at least some sets of the plurality of sets of optical filters, one or more skin biomarkers for the area of skin.

19. The method of claim 18, wherein the one or more skin biomarkers include at least one of:
melanin;
hemoglobin;
oxygenation; and
hydration.

20. The method of claim 13, wherein the optical filters of at least some of the sets of the plurality of sets of optical filters comprise interference filters.

* * * * *